(12) United States Patent
Gomm et al.

(10) Patent No.: US 10,191,072 B2
(45) Date of Patent: Jan. 29, 2019

(54) REAGENT AND SAMPLE HANDLING DEVICE FOR AUTOMATIC TESTING SYSTEM

(71) Applicant: Abbott Laboratories, Abbott Park, IL (US)

(72) Inventors: Cordell Kay Gomm, Mansfield, TX (US); Robert Paul Luoma, II, Colleyville, TX (US); David Charles Arnquist, The Colony, TX (US); Ryan Patrick Johnson, Lewisville, TX (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 14/731,060

(22) Filed: Jun. 4, 2015

(65) Prior Publication Data

US 2015/0268259 A1 Sep. 24, 2015

Related U.S. Application Data

(60) Continuation of application No. 12/612,791, filed on Nov. 5, 2009, now Pat. No. 9,057,714, which is a (Continued)

(51) Int. Cl.
*G01N 35/00* (2006.01)
*G01N 35/02* (2006.01)
*G01N 35/04* (2006.01)

(52) U.S. Cl.
CPC ... *G01N 35/00712* (2013.01); *G01N 35/0099* (2013.01); *G01N 35/00722* (2013.01); (Continued)

(58) Field of Classification Search
CPC .. G01N 35/00712; G01N 1/4022; G01N 1/44; G01N 35/00722; G01N 35/0099; G01N 2035/00316; G01N 2035/00049
See application file for complete search history.

(56) References Cited

U.S. PATENT DOCUMENTS 3,681,995 A 8/1972 Paatzsch
3,832,135 A 8/1974 Drozdowski
(Continued)

FOREIGN PATENT DOCUMENTS

EP 0435481 7/1991
EP 0452308 10/1991
(Continued)

OTHER PUBLICATIONS

European Patent Office, "Communication under Rule 71(3) EPC," issued in connection with European Patent Application No. 09152928. 9, dated Feb. 22, 2017, 44 pages.
(Continued)

*Primary Examiner* — Krishnan S Menon
*Assistant Examiner* — Dwan A Gerido
(74) *Attorney, Agent, or Firm* — Hanley, Flight & Zimmerman, LLC

(57) ABSTRACT

A handling device for samples and reagents to be used in testing in a system. Carriers of samples and reagents are loaded on a platform which detects the presence of, and proper loading of, such carriers. The carriers are moved from the platform by a transporter to a bar code reader for identification. A reagent container is rotated during reading to facilitate identification. The transporter further moves identified reagent carriers to a carousel on which the carriers automatically secured for storage awaiting use in testing. The carousel rotates, and selected reagent containers rotate on the rotating carousel, during storage.

17 Claims, 12 Drawing Sheets

Related U.S. Application Data division of application No. 11/122,280, filed on May 4, 2005, now Pat. No. 7,628,954.

(52) U.S. Cl.
CPC ........... *G01N 35/025* (2013.01); *G01N 35/04* (2013.01); *G01N 2035/00049* (2013.01); *G01N 2035/00316* (2013.01); *G01N 2035/00752* (2013.01); *G01N 2035/00891* (2013.01); *G01N 2035/0443* (2013.01); *G01N 2035/0491* (2013.01); *Y10S 901/01* (2013.01); *Y10T 436/11* (2015.01)

(56) References Cited

U.S. PATENT DOCUMENTS

| | | |
|---|---|---|
| 3,985,507 A | 10/1976 | Litz |
| 4,077,444 A | 3/1978 | Gilson et al. |
| 4,140,018 A | 2/1979 | Maldarelli et al. |
| 4,259,288 A | 3/1981 | Welch |
| RE30,627 E | 5/1981 | Bagshawe et al. |
| 4,276,258 A | 6/1981 | Ginsberg et al. |
| 4,298,570 A | 11/1981 | Lillig et al. |
| 4,299,796 A | 11/1981 | Esch |
| 4,322,216 A | 3/1982 | Lillig et al. |
| 4,328,185 A | 5/1982 | Reasons et al. |
| 4,338,279 A | 7/1982 | Orimo et al. |
| 4,363,782 A | 12/1982 | Yamashita |
| 4,420,191 A | 12/1983 | Arikawa et al. |
| 4,501,164 A | 2/1985 | Stockdale et al. |
| 4,517,160 A | 5/1985 | Galle et al. |
| 4,558,946 A | 12/1985 | Galle et al. |
| 4,582,990 A | 4/1986 | Stevens |
| 4,608,231 A | 8/1986 | Witty et al. |
| 4,634,576 A | 1/1987 | Galle et al. |
| 4,676,951 A | 6/1987 | Armes et al. |
| 4,678,752 A | 7/1987 | Thorne et al. |
| 4,678,894 A | 7/1987 | Shafer |
| 4,713,974 A | 12/1987 | Stone |
| 4,774,055 A | 9/1988 | Wakatake |
| 4,781,891 A | 11/1988 | Galle et al. |
| 4,785,407 A | 11/1988 | Sakagami |
| 4,844,868 A | 7/1989 | Rokugawa |
| 4,844,887 A | 7/1989 | Galle et al. |
| 4,848,917 A | 7/1989 | Benin et al. |
| 4,849,177 A | 7/1989 | Jordan |
| 4,882,283 A | 11/1989 | Gentry |
| 4,906,432 A | 3/1990 | Geiselman |
| 4,931,402 A | 6/1990 | Abplanalp |
| 4,948,563 A | 8/1990 | Kanewske, III |
| 4,956,148 A | 9/1990 | Grandone |
| 4,965,049 A | 10/1990 | Lillig et al. |
| 4,967,070 A | 10/1990 | Ringlien et al. |
| 5,035,861 A | 7/1991 | Grandone |
| 5,071,625 A | 12/1991 | Kelln |
| 5,087,423 A | 2/1992 | Ishibashi |
| 5,104,231 A | 4/1992 | Collier |
| 5,122,342 A | 6/1992 | McCulloch et al. |
| 5,147,610 A | 9/1992 | Watanabe et al. |
| 5,163,802 A | 11/1992 | Poinelli |
| 5,192,506 A | 3/1993 | Kureshy et al. |
| 5,201,232 A | 4/1993 | Uffenheimer |
| 5,240,678 A | 8/1993 | Litsche |
| 5,244,633 A | 9/1993 | Jakubowicz et al. |
| 5,250,440 A | 10/1993 | Kelln et al. |
| 5,254,315 A | 10/1993 | Nurse et al. |
| 5,260,872 A | 11/1993 | Copeland et al. |
| 5,266,272 A | 11/1993 | Griner et al. |
| 5,292,484 A | 3/1994 | Kelln et al. |
| 5,314,825 A | 5/1994 | Weyrauch et al. |
| 5,320,809 A | 6/1994 | Dunn et al. |
| 5,324,481 A | 6/1994 | Dunn et al. |
| 5,332,549 A | 7/1994 | MacIndoe, Jr. |
| 5,380,487 A | 1/1995 | Choperena et al. |
| 5,397,539 A | 3/1995 | Hayashi et al. |
| 5,402,875 A | 4/1995 | Markin et al. |
| 5,417,922 A | 5/1995 | Markin et al. |
| 5,483,843 A | 1/1996 | Miller et al. |
| 5,518,693 A | 5/1996 | Tomasso et al. |
| 5,525,304 A | 6/1996 | Matsson et al. |
| 5,525,515 A | 6/1996 | Blattner |
| 5,575,976 A | 11/1996 | Choperena et al. |
| 5,580,524 A | 12/1996 | Forrest et al. |
| 5,582,796 A | 12/1996 | Carey et al. |
| 5,587,129 A | 12/1996 | Kurosaki et al. |
| 5,591,642 A | 1/1997 | Jones |
| 5,594,230 A * | 1/1997 | Waite ................... G06K 7/10 235/462.15 |
| 5,601,783 A | 2/1997 | Breeser et al. |
| 5,605,665 A | 2/1997 | Clark et al. |
| 5,658,799 A | 8/1997 | Choperena et al. |
| 5,665,309 A | 9/1997 | Champseix et al. |
| 5,681,530 A | 10/1997 | Kuster |
| 5,693,292 A | 12/1997 | Choperena et al. |
| 5,700,429 A | 12/1997 | Bühler et al. |
| 5,728,954 A | 3/1998 | Uffenheimer |
| 5,730,938 A | 3/1998 | Carbonari et al. |
| 5,735,387 A | 4/1998 | Polaniec et al. |
| 5,736,102 A | 4/1998 | Seaton et al. |
| 5,744,099 A | 4/1998 | Chase et al. |
| 5,750,074 A | 5/1998 | Katzman et al. |
| 5,789,252 A | 8/1998 | Fujita et al. |
| 5,795,784 A | 8/1998 | Arnquist et al. |
| 5,841,039 A | 11/1998 | Uffenheimer |
| 5,853,667 A | 12/1998 | Seaton et al. |
| 5,876,670 A | 3/1999 | Mitsumaki et al. |
| 5,882,596 A | 3/1999 | Breeser et al. |
| 5,885,529 A | 3/1999 | Babson et al. |
| 5,885,530 A | 3/1999 | Babson et al. |
| 5,972,295 A | 10/1999 | Hanawa et al. |
| 6,019,945 A | 2/2000 | Ohishi et al. |
| 6,056,921 A | 5/2000 | Rao et al. |
| 6,060,022 A | 5/2000 | Pang et al. |
| 6,066,298 A | 5/2000 | Fukunaga |
| 6,071,477 A | 6/2000 | Auclair et al. |
| 6,081,326 A | 6/2000 | Rousseau et al. |
| 6,096,271 A | 8/2000 | Bogen et al. |
| 6,106,781 A | 8/2000 | Rosenberg |
| 6,149,872 A | 11/2000 | Mack et al. |
| 6,267,927 B1 | 7/2001 | Pomar Longedo et al. |
| 6,293,750 B1 | 9/2001 | Cohen et al. |
| 6,299,567 B1 | 10/2001 | Forrest et al. |
| 6,331,437 B1 | 12/2001 | Cohen et al. |
| 6,335,166 B1 | 1/2002 | Ammann et al. |
| 6,358,472 B1 | 3/2002 | DeYoung et al. |
| 6,403,035 B1 | 6/2002 | Caratsch et al. |
| 6,426,043 B1 | 7/2002 | Cohen et al. |
| 6,426,044 B1 | 7/2002 | Cohen et al. |
| 6,426,228 B1 | 7/2002 | Cohen et al. |
| 6,436,349 B1 | 8/2002 | Carey et al. |
| 6,440,368 B1 | 8/2002 | Cohen et al. |
| 6,444,472 B1 | 9/2002 | Cohen et al. |
| 6,451,259 B1 | 9/2002 | Cohen et al. |
| 6,489,169 B1 | 12/2002 | Cohen et al. |
| 6,521,183 B1 | 2/2003 | Burri et al. |
| 6,588,625 B2 | 7/2003 | Luoma, II et al. |
| 6,623,697 B2 | 9/2003 | Fuerst et al. |
| 6,691,748 B1 | 2/2004 | Tajima |
| 6,709,634 B1 | 3/2004 | Okada et al. |
| 6,723,288 B2 | 4/2004 | Devlin, Sr. et al. |
| 6,746,648 B1 | 6/2004 | Mattila et al. |
| 6,764,649 B2 | 7/2004 | Ammann |
| 6,776,961 B2 | 8/2004 | Lindsey et al. |
| 6,790,413 B2 | 9/2004 | Ngo et al. |
| 6,825,041 B2 | 11/2004 | Qureshi et al. |
| 6,843,357 B2 | 1/2005 | Bybee et al. |
| 6,890,485 B1 | 5/2005 | Stylli et al. |
| 7,132,082 B2 | 11/2006 | Aviles et al. |
| 7,407,627 B1 | 8/2008 | Rosenberg et al. |
| 7,458,483 B2 | 12/2008 | Luoma, II |
| 2002/0015665 A1 | 2/2002 | Lindsey et al. |
| 2002/0028157 A1 | 3/2002 | Takahashi et al. |
| 2002/0031837 A1 | 3/2002 | Matsubara et al. |
| 2002/0051736 A1 | 5/2002 | Zucker |

(56) References Cited

U.S. PATENT DOCUMENTS

| | | |
|---|---|---|
| 2002/0064884 A1 | 5/2002 | Devlin, Sr. et al. |
| 2002/0106801 A1 | 8/2002 | Matsubara et al. |
| 2002/0106802 A1 | 8/2002 | Matsubara et al. |
| 2002/0106814 A1 | 8/2002 | Matsubara et al. |
| 2002/0110917 A1 | 8/2002 | Matsubara et al. |
| 2002/0155590 A1 | 10/2002 | Gebrian et al. |
| 2002/0164269 A1 | 11/2002 | Ngo et al. |
| 2002/0169518 A1 | 11/2002 | Luoma, II et al. |
| 2003/0021728 A1 | 1/2003 | Sharpe, Jr. et al. |
| 2003/0026732 A1 | 2/2003 | Gordon et al. |
| 2003/0044323 A1 | 3/2003 | Diamond et al. |
| 2003/0054542 A1 | 3/2003 | Burns et al. |
| 2004/0005714 A1 | 1/2004 | Safar et al. |
| 2004/0057872 A1 | 3/2004 | Shibuya et al. |
| 2004/0091396 A1 | 5/2004 | Nakamura et al. |
| 2004/0096368 A1 | 5/2004 | Davis et al. |
| 2004/0109791 A1 | 6/2004 | Itoh |
| 2004/0131499 A1 | 7/2004 | Okada et al. |
| 2004/0134750 A1* | 7/2004 | Luoma, II ............... B01L 9/00 198/340 |
| 2004/0208787 A1 | 10/2004 | Takahashi et al. |
| 2004/0253146 A1 | 12/2004 | Shiba et al. |
| 2005/0005968 A1 | 1/2005 | Berry et al. |
| 2005/0013735 A1 | 1/2005 | Gebrian et al. |
| 2005/0013736 A1 | 1/2005 | McKeever |
| 2005/0013737 A1 | 1/2005 | Chow et al. |
| 2005/0047964 A1 | 3/2005 | Nishida et al. |
| 2005/0089444 A1 | 4/2005 | Justin et al. |
| 2006/0093529 A1 | 5/2006 | Meyer et al. |
| 2006/0159587 A1 | 7/2006 | Fechtner et al. |
| 2006/0167580 A1 | 7/2006 | Whittier |
| 2006/0210433 A1* | 9/2006 | Lair ..................... C12Q 1/6851 422/63 |
| 2007/0010019 A1 | 1/2007 | Luoma, II |
| 2008/0190735 A1 | 8/2008 | Luoma |

FOREIGN PATENT DOCUMENTS

| | | |
|---|---|---|
| EP | 0471981 | 2/1992 |
| EP | 0502638 | 9/1992 |
| EP | 0525577 | 2/1993 |
| EP | 0564970 | 10/1993 |
| EP | 0567093 | 10/1993 |
| EP | 0628824 | 12/1994 |
| EP | 0632271 | 1/1995 |
| EP | 0755519 | 1/1997 |
| EP | 0769547 | 4/1997 |
| EP | 0809112 | 11/1997 |
| EP | 0867724 | 9/1998 |
| EP | 0918221 | 5/1999 |
| EP | 0937983 | 8/1999 |
| EP | 0973039 | 1/2000 |
| EP | 0979999 | 2/2000 |
| EP | 0990906 | 4/2000 |
| EP | 1052513 | 11/2000 |
| EP | 1058826 | 12/2000 |
| EP | 1099950 | 5/2001 |
| EP | 1248113 | 10/2002 |
| EP | 1398613 | 3/2004 |
| EP | 1460431 | 9/2004 |
| EP | 1498734 | 1/2005 |
| EP | 2175279 | 4/2010 |
| GB | 1354286 | 5/1974 |
| JP | S61160036 | 7/1986 |
| JP | S6298262 | 5/1987 |
| JP | 01250759 | 10/1989 |
| JP | 03183957 | 8/1991 |
| JP | 04172252 | 6/1992 |
| JP | 06034642 | 2/1994 |
| JP | 6-25944 | 4/1994 |
| JP | H06242125 | 9/1994 |
| JP | 2000046842 | 2/2000 |
| JP | 2000081439 | 3/2000 |
| JP | 2001099841 | 4/2001 |
| JP | 2010156716 | 7/2010 |
| WO | 90/08307 | 7/1990 |
| WO | 92/22800 | 12/1992 |
| WO | 92/22801 | 12/1992 |
| WO | 92/22802 | 12/1992 |
| WO | 92/22879 | 12/1992 |
| WO | 92/22880 | 12/1992 |
| WO | 93/20440 | 10/1993 |
| WO | 97/16733 | 5/1997 |
| WO | 97/26541 | 7/1997 |
| WO | 98/21595 | 5/1998 |
| WO | 98/57739 | 12/1998 |
| WO | 99/44031 | 9/1999 |
| WO | 01/36981 | 5/2001 |
| WO | 01/96863 | 12/2001 |
| WO | 02/08769 | 1/2002 |
| WO | 02/086514 | 10/2002 |
| WO | 03/012453 | 2/2003 |
| WO | 03/036273 | 5/2003 |
| WO | 03/093833 | 11/2003 |
| WO | 2004/013640 | 2/2004 |
| WO | 2005/005992 | 1/2005 |
| WO | 2005/116613 | 12/2005 |

OTHER PUBLICATIONS

Canadian Intellectual Property Office, "Notice of Allowance," issued in connection with Canadian Patent Application No. 2,606,050, dated Apr. 27, 2017, 1 page.

Notification of Reasons(s) for Rejection, with English version, issued by the Japanese Intellectual Property Office in connection with Japanese Patent Application No. 2008510163, dated Aug. 2, 2011, 4 pages.

Notification of Reasons(s) for Rejection, with English version, issued by the Japanese Intellectual Property Office in connection with Japanese Patent Application No. 2012019531, dated Aug. 27, 2013, 5 pages.

Notice for Reasons for Rejection, English Language version, issued by the Intellectual Property Office of Japan, in connection with Japanese application No. 2012-019531, dated Mar. 11, 2014, 2 pages.

International Search Report, issued by the International Searching Authority in connection with PCT Application No. PCT/US2006/016976, dated Mar. 6, 2007, 5 pages.

International Preliminary Report on Patentability and Written Opinion, issued by the International Searching Authority in connection with PCT Application No. PCT/US2006/016976, dated Nov. 6, 2007, 9 pages.

European Office Action, issued by the European Patent Office in connection with European Patent Application No. 09152928.9, dated Jul. 16, 2013, 6 pages.

Office Action, issued by the Canadian Intellectual Property Office in connection with Canadian Patent Application No. 2,606,050 dated Sep. 4, 2013, 2 pages.

Canadian Office Action. issued by the Canadian Intellectual Property Office. In connection with corresponding Canadian patent application No. 2,606,050, dated Jul. 30, 2014, 2 pages.

Office Action, issued by the United States Patent and Trademark Office in connection with U.S. Appl. No. 11/122,280, dated Jan. 27, 2009, 8 pages.

Notice of Allowance and Fee(s) Due, issued by the United States Patent and Trademark Office in connection with U.S. Appl. No. 11/122,280, dated Aug. 18, 2009, 6 pages.

Office Action, issued by the United States Patent and Trademark Office in connection with U.S. Appl. No. 12/612,791, dated Jul. 7, 2010, 7 pages.

Final Rejection, issued by the United States Patent and Trademark Office in connection with U.S. Appl. No. 12/612,791, dated Jan. 10, 2011, 7 pages.

Final Rejection, issued by the United States Patent and Trademark Office in connection with U.S. Appl. No. 12/612,791, dated Aug. 10, 2012, 9 pages.

(56) References Cited

OTHER PUBLICATIONS

Office Action, issued by the United States Patent and Trademark Office in connection with U.S. Appl. No. 12/612,791, dated Jul. 1, 2013, 8 pages.
Final Rejection, issued by the United States Patent and Trademark Office in connection with U.S. Appl. No. 12/612,791, dated Jan. 21, 2014, 11 pages.
Office Action, issued by the United States Patent and Trademark Office in connection with U.S. Appl. No. 12/612,791, dated Jul. 15, 2014, 10 pages.
Notice of Allowance and Fee(s) Due, issued by the United States Patent and Trademark Office in connection with U.S. Appl. No. 12/612,791, dated Feb. 10, 2015, 7 pages.
European Patent Office, "Extended European Search Report," issued in connection with European Patent Application No. 17184628.0, dated Dec. 7, 2017, 10 pages.
Canadian Intellectual Property Office, "Office Action," issued in connection with Canadian Patent Application No. 2,947,790, dated Sep. 5, 2017, 4 pages.
Canadian Intellectual Property Office, "Office Action," issued in connection with Canadian Patent Application No. 2,947,790, dated Jul. 23, 2018, 4 pages.

\* cited by examiner

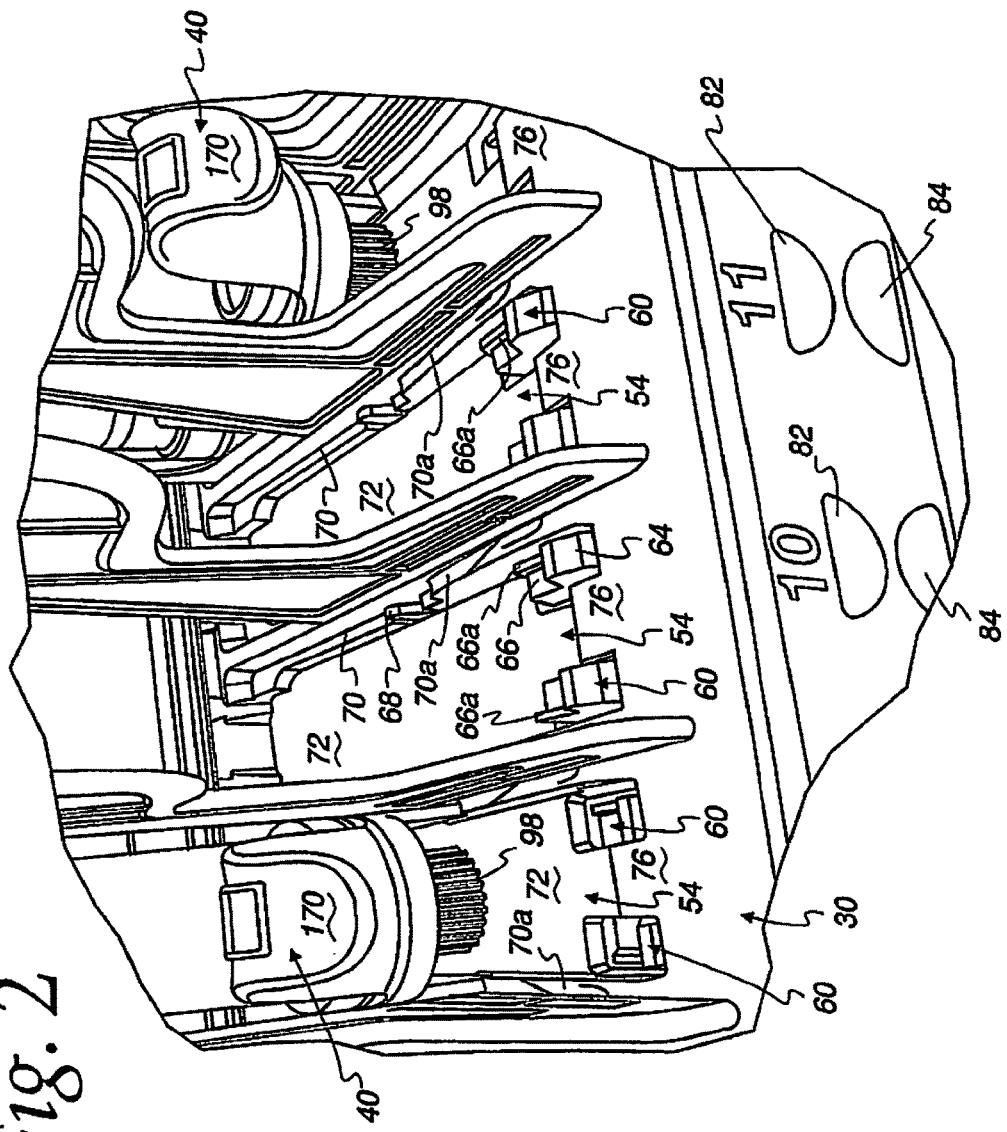
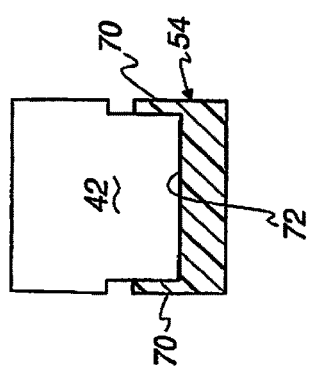
Fig. 2
Fig. 2a
Fig. 2b

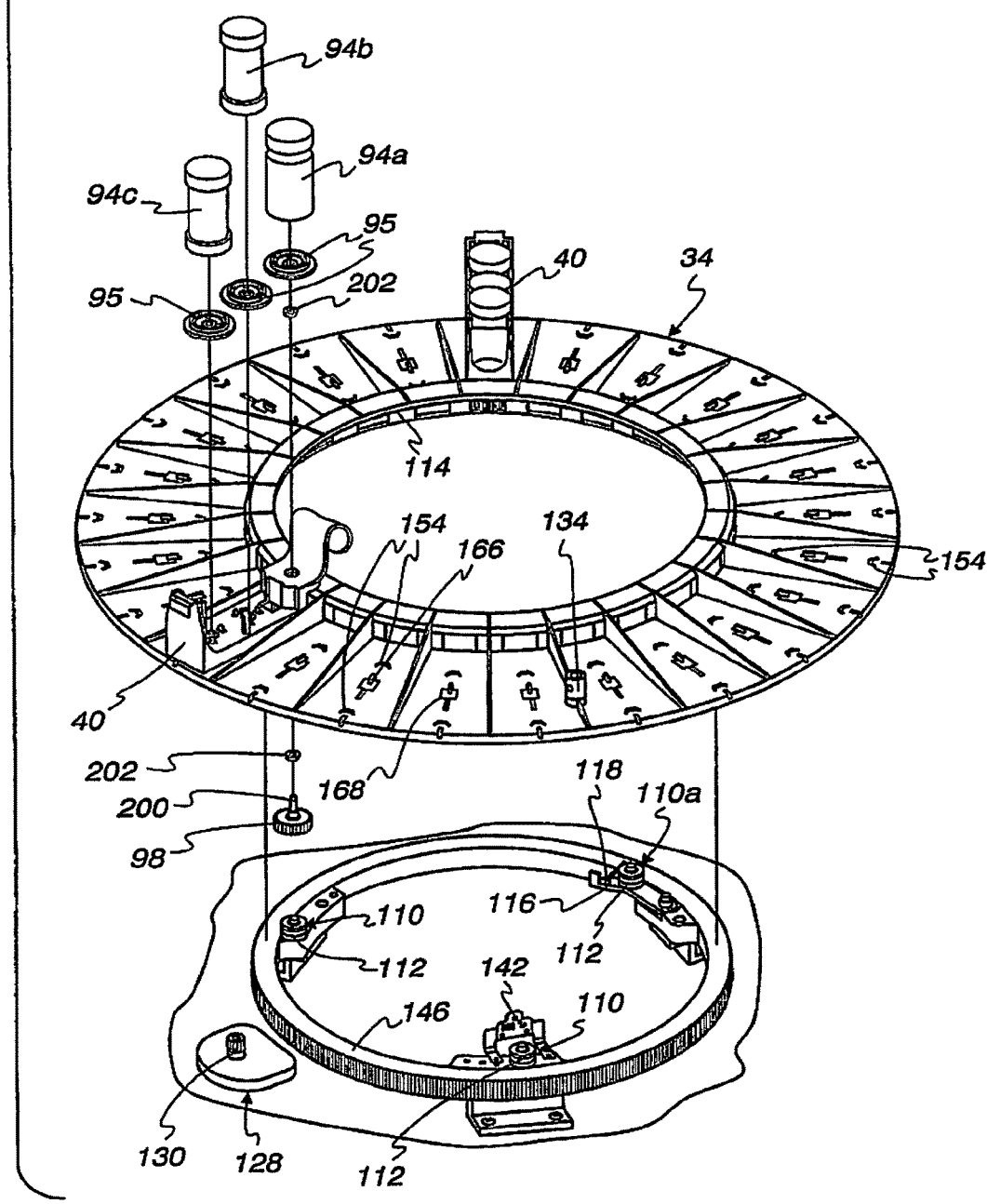

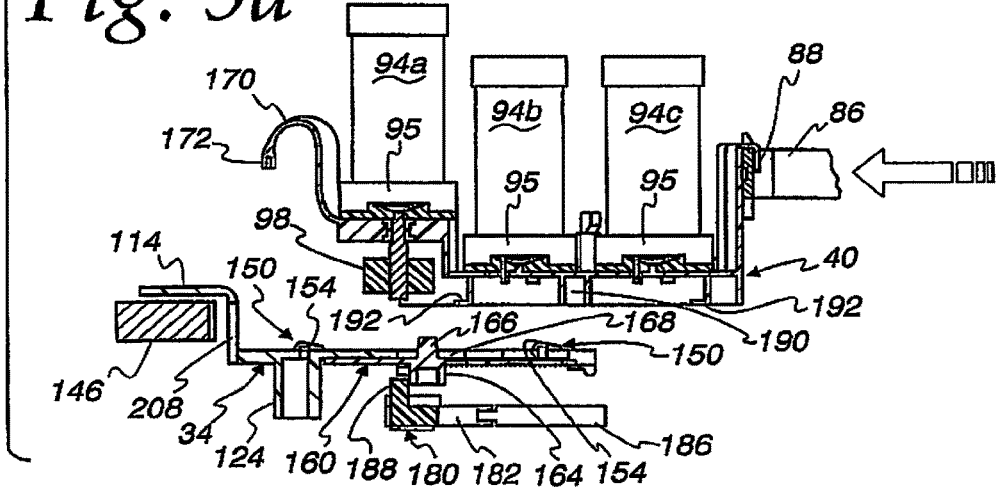
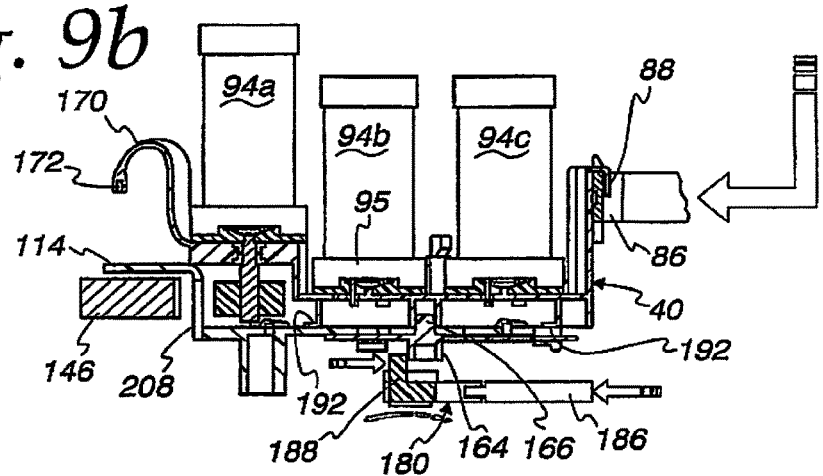
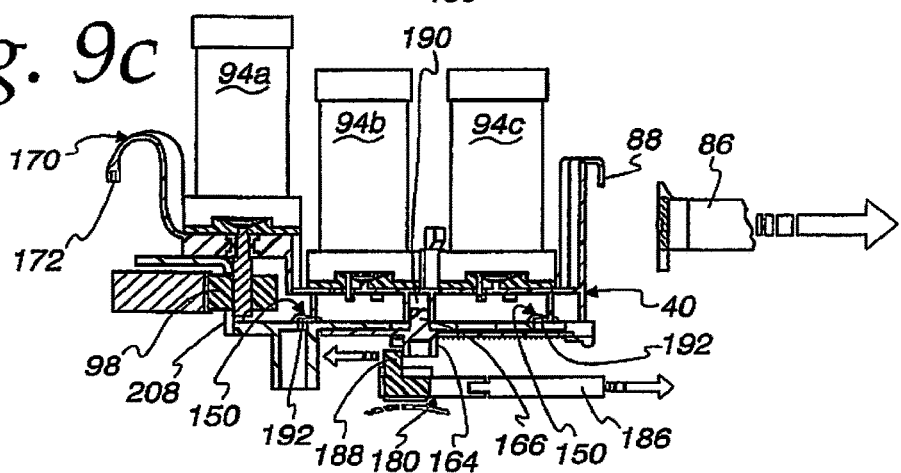

REAGENT AND SAMPLE HANDLING DEVICE FOR AUTOMATIC TESTING SYSTEM

RELATED APPLICATIONS

This patent arises from a continuation of U.S. patent application Ser. No. 12/612,791 (now U.S. Pat. No. 9,057,714), filed Nov. 5, 2009, which is a divisional application of U.S. patent application Ser. No. 11/122,280 (now U.S. Pat. No. 7,628,954), filed May 4, 2005. U.S. patent application Ser. No. 12/612,791 and U.S. patent application Ser. No. 11/122,280 are hereby incorporated by reference in their entireties.

FIELD OF THE DISCLOSURE

The present invention is directed toward testing of specimens, and particularly toward an apparatus for automatically handling fluids such as reagents which are to be used for such testing.

BACKGROUND

Testing sample biological specimens is commonly done to, for example, check for the presence of an item of interest, which item may be or include all or portions of a specific region of DNA, RNA, fragments, complements, peptides, polypeptides, enzymes, prions, proteins, messenger RNA, transfer RNA, mitochondrial RNA or DNA, antibodies, antigens, allergens, parts of biological entities such as cells, virons or the like, surface proteins, functional equivalents of the above, etc. Specimens such as a patient's body fluids (e.g., serum, whole blood, urine, swabs, plasma, cerebraspinal fluid, lymph fluids, tissue solids) can be analyzed using a number of different tests to provide information about a patient's health.

In such testing, it is imperative that the specimens be handled in a manner which prevents contaminants from being introduced to the specimens, whether from the outside environment or between specimens. Obviously, where the HIV virus from one specimen is inadvertently allowed to contaminate the specimen of a different patient, the resulting false positive test result could potentially have catastrophic psychological effect on the patient, even should subsequent testing later discover the error. Moreover, since such testing is highly sensitive, even the smallest amounts of contamination can cause erroneous test results. In such sophisticated testing, it is also imperative that the various reagents which may be used in the testing be properly handled as well, not only to avoid contaminants but also to ensure that the proper reagent in proper quantities is used at appropriate times.

Commonly, such testing is accomplished using automated devices which handle multiple specimens and fluids (typically, reagents). For example, U.S. Pat. No. 6,588,625 B2 and U.S. Application Publication No. 2004/0005714 A1 (the disclosures of which are hereby incorporated by reference) variously disclose systems for handling fluids and specimens of this type.

Such automated devices often use sets of pipettes to move various fluids between their original containers (usually receptacles such as open topped tubes) and containers in which the specimens are to be processed. For example, a specimen may be contained in a tube loaded in a rack on the device, and a head carrying a pipette will through programmed motion move the pipettes into that tube, where a vacuum will be applied to extract a selected amount of the specimen from the tube into the pipette. The head will then retract the pipette from the tube and move over to another tube or reaction vessel located at a processing station, depositing the extracted amount of the specimen from the pipette into the reaction vessel. A similar process may be followed to acquire an appropriate reagent (depending upon the desired test) from a reagent supply.

At the processing station of such automated devices, the specimens are variously handled according to the purpose of the testing (e.g., incubated, prepared, lysed, eluted, analyzed, read, etc.). For example, the specimens may be prepared for analyzing, as for example by separating DNA or RNA from the specimen. The specimens may also or alternatively be analyzed. Commonly, such processes involve the addition of various fluids (typically reagents) to the specimen in each tube. For example, in a first step, a reagent may be added to each of the tubes to wash the specimens, and second and third (and more) reagents may be added to the specimens in the course of carrying out other processes to, for example, unbind and/or separate the DNA or RNA of interest allow so that it may be extracted from the specimen in each tube for subsequent testing. Similar processes, in which the same or different reagents are added to the tubes, may also occur after the specimen has been prepared as a part of the analyzing of the prepared specimens.

The handling of the reagents and other fluids can, with such automated devices, be problematic. Though the reagents can be automatically moved from receptacles to the specimen containing tubes in the processing station by use of the head and pipettes such as noted, it is in the first instance necessary to load the appropriate reagent into the appropriate receptacle on the device in order to ensure that the head and pipettes are adding the appropriate reagent to the appropriate specimen containing tube at the appropriate time in the process.

Heretofore, loading the appropriate reagent into the appropriate receptacle has been accomplished in several different ways. In one such procedure, the individual who is controlling the device manually measures and adds the reagents to receptacles, and then places those receptacles on the device. In another such procedure, the loading of reagents is automatically accomplished by the device itself, which uses some transfer apparatus (such as a head and pipette(s) as previously described) to move the reagents from bulk supplies of the reagents provided with the device. However, either of the above procedures can be problematic. For example, manually adding the reagents can introduce human error, such as mounting the reagent receptacle incorrectly on the device. Moreover, even if the reagents are correctly loaded in the correct amounts, they may be loaded at the wrong location on the device so that when the head and pipettes automatically draw a reagent for use at a certain step of the processing, it may well be the wrong reagent, or there could be no reagent of any kind where the head and pipettes go to extract it.

The Architect7 i2000 systems of Abbott Laboratories of Abbott Park, Ill. is a high throughput analyzer providing automated operation in which the operator may be freed from interacting with the analyzer for long periods of time. With that device, bulk supplies of reagents can be manually loaded onto a refrigerated carousel, with the analyzer then automatically obtaining the desired samples and reagents for the processing station at which testing procedures are accomplished. The containers for the reagents and samples are barcoded for automatic tracking on the system. Each reagent container can contain sufficient reagents for many tests so that, depending upon usage and the types of tests most commonly performed, some reagent containers can be maintained on the carousel for long periods of time. Particularly for reagents which are made with suspended microparticles, consistent use and dosages may be negatively impacted due to settling of the microparticles over time.

The present invention is directed to improving upon the reagent and sample handling devices of the prior art testing systems such as described above.

SUMMARY

In one aspect of the present invention, a handling device for samples and reagents to be used in testing in a system is provided, including at least one carrier for reagent containers, at least one carrier for sample containers, and a platform defining a plurality of locations on which the containers may be placed from a loading side for loading into the testing system. A position indicator at each location is biased upwardly toward a first position and cooperates with the platform whereby the position indicator is engaged by a carrier on the associated position of the platform wherein (a) the position indicator is in a second position when any carrier is only partially loaded at the associated location, (b) the position indicator is in a third position when a sample carrier is properly loaded at the associated location, and (c) the position indicator is in a fourth position when a reagent carrier is properly loaded at the associated location. A sensor detects the position of the position indicator.

In one form of this aspect of the invention, the sensor consists of first and second proximity sensors and the position indicator includes first and second ears aligned with the first and second proximity sensors, respectively. In the first position, the ears are spaced from the proximity sensors; in the second position, the first ear is proximate the first proximity sensor and the second ear is spaced from the second proximity sensor; in the third position, the first ear is proximate the first proximity sensor and the second ear is proximate the second proximity sensor; and in the fourth position, the first ear is spaced from the first proximity sensor and the second ear is proximate the second proximity sensor. In one further form, the position indicator is pivotally secured beneath the platform on one end and the ears are disposed on the other end of the position indicator. In another further form, the proximity sensors are electric eyes, and the ears are detected as proximate thereto when the electric eyes are blocked.

In another form of this aspect of the invention, the platform includes openings therethrough at each carrier location of the platform, and the position indicator includes projections extending through the openings and adapted to be selectively engaged by a sample carrier or reagent carrier in either a partially loaded position or a properly loaded position.

In a further form, the platform at each location includes a flat portion and a raised end at the loading side, and the projections include first and second knuckles. The first knuckle projects above the platform raised end a first distance when the position indicator is in the first position, and the second knuckle projects above the platform flat portion a second distance when the position indicator is in the first position. A partially loaded carrier rests on the raised end and engages the first knuckle to force the position indicator down the first distance to the second position, and one of the sample and reagent carriers when properly loaded on the platform engages the second knuckle to force the position indicator down the second distance to one of the third and fourth positions.

In a still further form, the platform locations include raised ledges along opposite sides of the platform flat portion, the raised ledges being adapted to support the other of the sample and reagent carriers above the flat portion when properly loaded. A third knuckle projects above the ledges a third distance when the position indicator is in the first position, whereby the other of the sample and reagent carriers when properly loaded on the platform engages the third knuckle to force the position indicator down the third distance to the other of the third and fourth positions.

In yet a further form, the third distance is greater than the second distance and the second distance is greater than the first distance.

In yet another further form, the sensor comprises first and second proximity sensors and the position indicator (a) is spaced from the proximity sensors in the first position, (b) is proximate the first proximity sensor and is spaced from the second proximity sensor in the second position, (c) is proximate both the first and second proximity sensors in the third position, and (d) is spaced from the first proximity sensor and proximate the second proximity sensor in the fourth position. In a further form, the proximity sensors are electric eyes, and the ears are detected as proximate thereto when the electric eyes are blocked.

In another aspect of the present invention, a carrier is provided which is usable in a biological testing system having a transporter adapted to move the carrier between a loading platform and an active storage carousel. The carrier includes a base member adapted to be received on the loading platform for loading the carrier into the testing system, at least one bottle seat rotatably mountable on one end of a pivot shaft through the base member, where the bottle seat is adapted to securely seat a container for a reagent usable in biological testing, and a drive member secured beneath the base member to the other end of the pivot shaft, wherein the drive member and bottle seat rotate together.

In one form of this aspect of the invention, the drive member is a gear.

In still another aspect of the present invention, a supply mechanism for a biological testing system is provided, including a loading platform, a carrier, a bar code reader, and a transporter. The carrier has a base member adapted to be received on the loading platform for loading the carrier into the testing system, at least one bottle seat rotatably mountable on one end of a pivot shaft through the base member, where the bottle seat is adapted to securely seat a container for a reagent usable in biological testing, and a drive member secured beneath the base member to the other end of the pivot shaft, wherein the drive member and bottle seat rotate together. The transporter is adapted to pick up the carrier at the loading platform and move the carrier to the bar code reader for reading a bar code identifying the reagent bottle seated on the one bottle seat. A drive adjacent the bar code reader is adapted to engage the carrier drive member when the reagent bottle seated on the one bottle seat is in position for its identifying bar code to be read by the bar code reader.

In yet another aspect of the present invention, a supply mechanism for a biological testing system is provided, including a storage carousel rotatably drivable about an axis, the carousel having storage locations therearound generally radially oriented relative to the axis, a plurality of carriers releasably securable on selected carousel storage locations, and a ring gear substantially centered on the axis. Each of the carriers has a base member adapted to be received on the loading platform for loading the carrier into the testing system, at least one bottle seat rotatably mountable on one end of a pivot shaft through the base member, the at least one bottle seat adapted to securely seat a container for a reagent usable in biological testing, and a drive member secured beneath the base member to the other end of the pivot shaft, wherein the drive member and at least one bottle seat rotate together. The ring gear engages the drive members of carriers secured to the carousel whereby rotation of the carousel about the axis rotates the bottle seat seats about the pivot shafts of the carriers to agitate reagent in seated containers.

In still another aspect of the present invention, a supply mechanism for a biological testing system is provided, including a storage carousel rotatably drivable about an axis, the carousel having storage locations therearound generally radially oriented relative to the axis, a plurality of carriers releasably securable on carousel storage locations, a transporter adapted to transport carriers to and from the carousel storage location located at a transfer station, a connector at each of the carousel storage locations for connecting the carriers to the carousel, and a release control adjacent the transfer station adapted to release the connection when the transporter is adjacent the transfer station.

In one form of this aspect of the present invention, the connector includes at least one pocket at each carousel storage location adapted to receive a tab on a loaded carrier to secure the carrier to the storage location, and a connecting member at each carousel storage location. The connecting member is biased in a first direction toward moving a carrier located in the carousel storage location to a position in which its tab is received in the pocket. The release control is engaged by the transporter to move the connecting member in a direction opposite the first direction to free the tab from the pocket when the transporter is adjacent the transfer station. In a further form, the release control is a lever actuated by the transporter to engage and move the connecting member of the storage location at the transfer station in the opposite direction. In another further form, a spring biases the connecting members in the first direction.

In another form of this aspect of the present invention, a bar code reader and a loading platform are provided. In this form, each of the carriers have a base member adapted to be received on the loading platform for loading the carrier into the testing system, at least one bottle seat rotatably mountable on one end of a pivot shaft through the base member, the bottle seat adapted to securely seat a container for a reagent usable in biological testing, and a drive member secured beneath the base member to the other end of the pivot shaft, wherein the drive member and bottle seat rotate together. Further, the transporter is adapted to pick up the carrier at the loading platform and move the carrier to the bar code reader for reading a bar code identifying the reagent bottle seated on the at least one bottle seat. This form further includes a ring gear substantially centered on the carousel axis, and a drive adjacent the bar code reader. The ring gear engages the drive members of carriers secured to the carousel whereby rotation of the carousel about the axis rotates the bottle seats about the pivot shafts of the carriers to agitate reagent in seated containers. Further, the drive adjacent the bar code reader is adapted to engage the carrier drive member when the reagent bottle seated on the one bottle seat is in position for its identifying bar code to be read by the bar code reader.

BRIEF DESCRIPTION OF THE DRAWINGS

FIG. 2 is a perspective view of a portion of a load platform according to the present invention;

FIG. 2a is a simplified view of a sample carrier on the load platform;

FIG. 2b is a simplified view of a reagent carrier on the load platform;

FIG. 6 is an exploded view of the carousel portion of the handling device of the present invention;

FIGS. 9a to 9c are cross-sectional views illustrating the loading of a reagent carrier onto the carousel.

DETAILED DESCRIPTION

Figure 1:
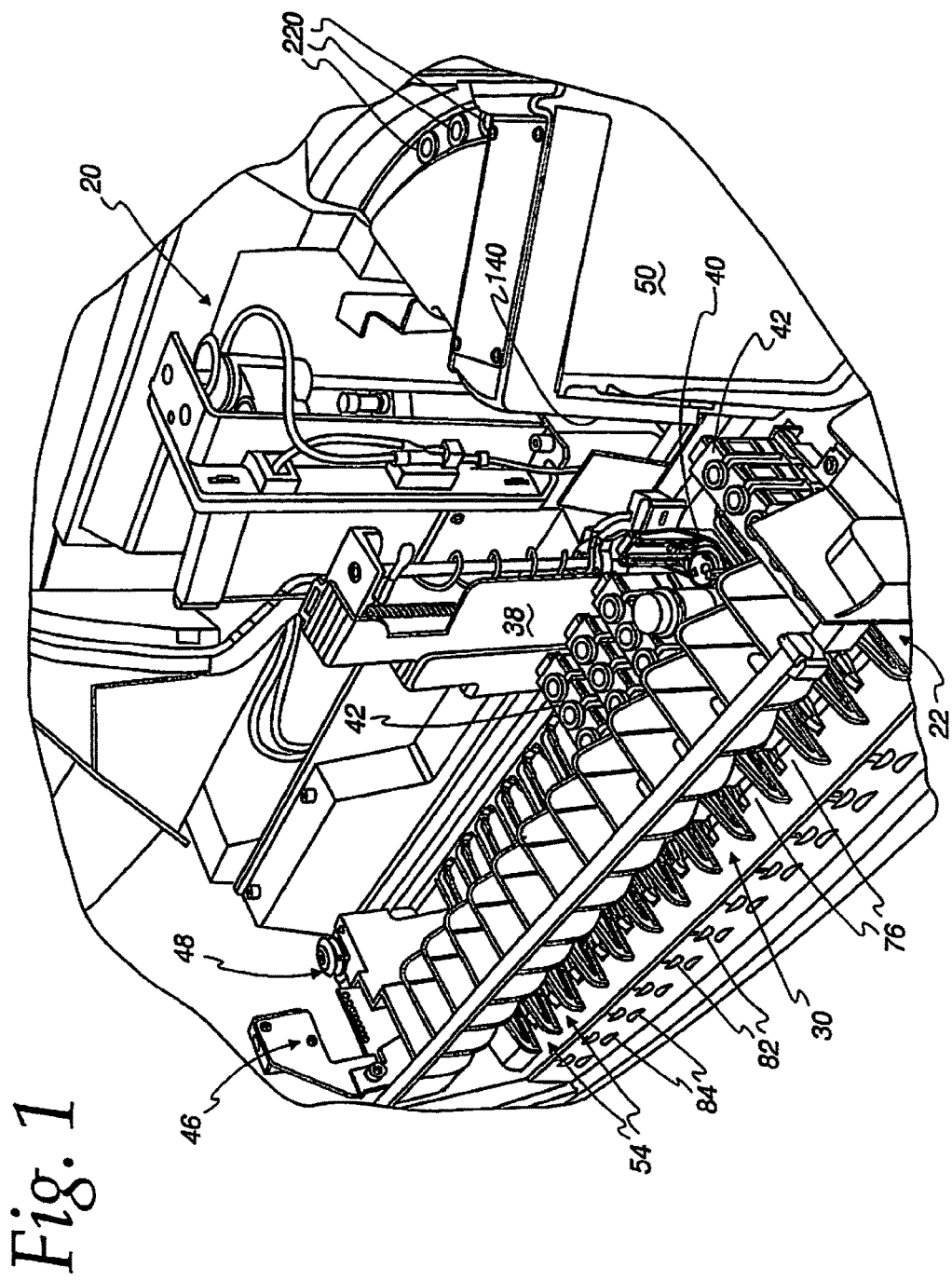
FIG. 1 is a perspective view of a portion of a testing system having the reagent and sample handling device of the present invention.

A testing system 20 such as may be used in biological testing of samples is shown in part in FIG. 1, and in particular a handling device 22 for handling samples and reagents to be used in the testing is illustrated. The present invention relates particularly to the handling device 22, which may most advantageously be used with automatic testing systems requiring minimal operator intervention. In particular, the various features of the handling device 22 of the present invention facilitate the handling of samples and reagents whereby the samples and reagents may be simply and reliably loaded into the testing system 20 and thereafter reliably and automatically handled so as to be properly input to the desired testing sequences.

The various features of the handling device 22 of the present invention are variously provided in a load platform 30, a reagent carousel 34, a transporter or transport carrier 38, reagent carriers 40, and sample carriers 42.

As a brief overview, an operator loads samples into suitable bottles or containers secured to the sample carriers 42 and/or loads reagents into suitable bottles or containers secured to the reagent carriers 40, and then places the loaded carrier (40 and/or 42) onto the load platform 30. (It should be appreciated that while the description herein illustrates containers which are separate from, and carried by, carriers 40, 42, single components which are integral carrier and containers could be advantageously used within the scope of many aspects of the present invention. That is, it could be within the scope of the present invention to provide containers which themselves are configured to be suitably handled as described herein, and it is not required that the function of the containers and carriers be provided by separate components.)

As described in detail below, the handling device 22 recognizes what type of carrier 40, 42 is loaded, and whether it has been properly loaded. When a properly loaded carrier 40, 42 is detected, it is automatically picked up by the transporter 38 and moved to a suitable bar code reader 46 which reads the bar codes on the containers and/or carriers 40, 42 to input such data into a control for the system 20 (e.g., a computer terminal allowing for operator input to control the system 20 for performing desired actions, such as is known in the art).

When the carrier is a sample carrier 42, the transporter 38 may then return the carrier to the load platform 30, or place it in a ready position for accessing by the testing system 20.

When the carrier is a reagent carrier 40, a motor drive 48 adjacent the bar code reader 46 is engaged to cause a selected one of the reagent containers to rotate to facilitate reading of its bar code by the bar code reader 46. The reagent carrier 40 (with its contents thus identified for the system 20) is then carried by the transporter 38 to a ready storage location and mounting on the carousel 34 located therein. As illustrated in FIG. 1, a housing 50 is located adjacent one end of the load platform 30 (the end opposite the bar code reader 46) and the carousel 34 (not visible in FIG. 1) is enclosed therein. Reagents may be stored on the carousel 34 for long periods of time, waiting to be used when a test requiring such reagent is called for by the operator. Moreover, each reagent container may contain sufficient reagent to perform multiple tests (e.g., 50 or 100 tests), and thus the reagent containers may be maintained in the housing 50 until used up with that number of tests. Because of such storage requirements, the interior of the housing 50 may be suitably cooled so as to define a refrigerated compartment therein to properly store the various reagents during such time.

Testing by the testing system 20 may be accomplished by any suitable means which picks up the particular required samples and reagents (e.g., by a pipettor or other aspiration system which draws the samples and reagents from their containers) and then moves the samples and reagents to the testing area, where they are, for example, added to suitable reaction vessels which are processed as appropriate for the particular test desired. Any such testing system 20 may be advantageously used with the present invention, and details of such system 20 do not form a part of the present invention.

Reference will now be had to particular components of the present invention.

The load platform 30 is seen in FIG. 1, and is variously shown in greater detail in FIGS. 2 to 5h, and includes a plurality of different locations 54 at which carriers 40, 42 may be manually loaded by an operator. For example, FIG. 2 illustrates a portion of the load platform 30 having four locations 54, two of which are empty (locations "10" and "11") and two of which have reagent carriers 40 loaded therein.

The load platform 30 may advantageously cooperate with the carriers 40, 42 to automatically detect the presence or absence of a carrier 40, 42 at a particular location 54, the type of carrier 40, 42 and whether the operator has manually loaded the carrier 40, 42 properly in the location. Specifically, a position indicator 60 is provided at each location 54 for detecting the position of anything placed in the associated location 54. A structure which may be advantageously used for this purpose in connection with the present invention is best illustrated in FIGS. 2 to 4d.

The position indicator 60 is pivotally secured to the underside of the load platform 30 near the rear of each location 54, and a suitable spring 62 biases the position indicator 60 up against the bottom of the load platform 30. Openings are provided in the platform 30 through which projecting portions or knuckles 64, 66, 68 of the position indicator 60 project as best seen in FIG. 2. As also best seen in FIG. 2, the knuckles 66 may also include a raised side wall 66a.

Raised ledges 70 are provided on opposite sides of each platform location 54, and the bottom of the reagent and sample carriers 40, 42 are differently configured whereby the bottom of the sample carriers 42 are narrower than the spacing between the ledges 70 so that they will rest on the bottom 72 of the platform location when properly loaded therein (see FIG. 2a), whereas the reagent carriers 40 will be supported above the platform location bottom 72 by the ledges 70 (see FIG. 2b).

Moreover, one set of knuckles 64 is located forwardmost of the platform 30, projecting above a raised front portion 76 of the platform a selected amount. It should be appreciated that a carrier 40, 42 which is not pushed into the location 54 sufficiently so as to be past the raised front portion 76 will rest on the knuckles 64 and push the position indicator 60 down that selected amount.

The second set of knuckles 66 is positioned rearwardly of the platform raised front portion 76 and extends above the platform location bottom 72 by a different selected amount. These knuckles 66 are spaced from the rear of the platform location 54 a distance substantially equal to the depth of a sample carrier 42. Accordingly, when a sample carrier 42 is properly loaded in the position 54 (resting on the platform location bottom 72), it will be past the raised front portion 76 and rest on the second set of knuckles 66 (between the side walls 66a), thereby pushing the position indicator 60 down against the bias of the spring 62 that different selected amount.

The third set of knuckles 68 extend upwardly through openings in the raised ledges 70. The third set of knuckles 68 are spaced still further back from the platform front and, when a reagent carrier 40 is properly loaded in the platform location 54, it will rest on these knuckles 68 to push the position indicator 60 down against the bias of the spring 62 yet another selected amount. Still further, it should be appreciated that if the reagent carrier 40 is not sufficiently pushed into the platform location 54, it may rest either on the first set of knuckles 66, or on the side walls 66a of the second set of knuckles 66, or (as illustrated in FIG. 3b) on a front raised portion 70a of the ledges 70 (see FIG. 2) to in all cases push the position indicator 60 down about the same amount.

It should be appreciated that the selected distances which the position indicator 60 may be pushed down in different conditions may be different from the particular described embodiment herein. Further, it should be understood that where the position indicator 60 is pivoted at one end as in the illustrated embodiment, the distance which a particular set of knuckles projects up to provide a particular displacement at the opposite end of the position indicator 60 will be dependent upon the distance of the knuckles from the pivot axis. In short, it should be understood that the relative positions and distances as illustrated for the knuckles 64, 66, 66a, 68 of the illustrated embodiment could readily be varied in accordance with the present invention.

Depending upon the type of carrier 40, 42 and its position in a location 54 of the platform 30, the position indicator 60 will be variously pushed down to different positions against the biasing force of the spring 62, and the particular position of the position indicator 60 can be automatically detected to determine that information, as best illustrated in FIGS. 3a to 4d.

Specifically, FIGS. 3a to 4d illustrate one advantageous manner in which the different positions of the position indicator 60 may be determined to advantageously provide feedback to the system 20 as to the presence or not of a particular carrier 40, 42 at each platform location 54. Specifically, two projections or ears 80a, 80b are provided on an end face of the position indicator 60 remote from its pivot. The ears 80a, 80b are aligned with two proximity sensors 82a, 82b (e.g., electric eyes) fixed at the front of each platform location 54.

Figure 3A:
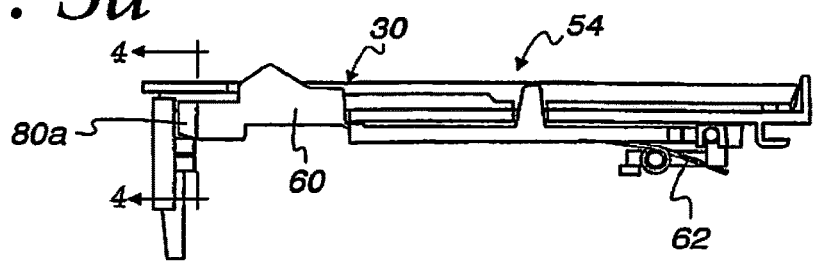
FIG. 3a is a side view of a load platform location with no carrier loaded thereon.
Figure 3B:
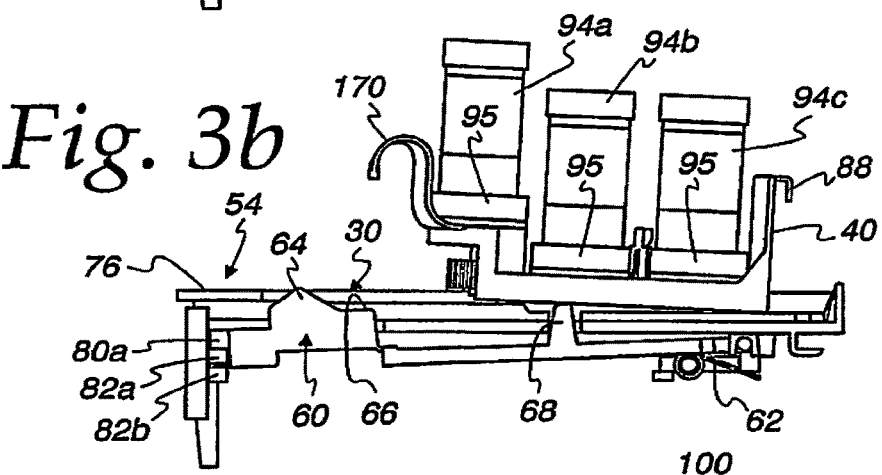
FIG. 3b is a side view of a load platform location with a reagent carrier at the location but not fully inserted.
Figure 3C:
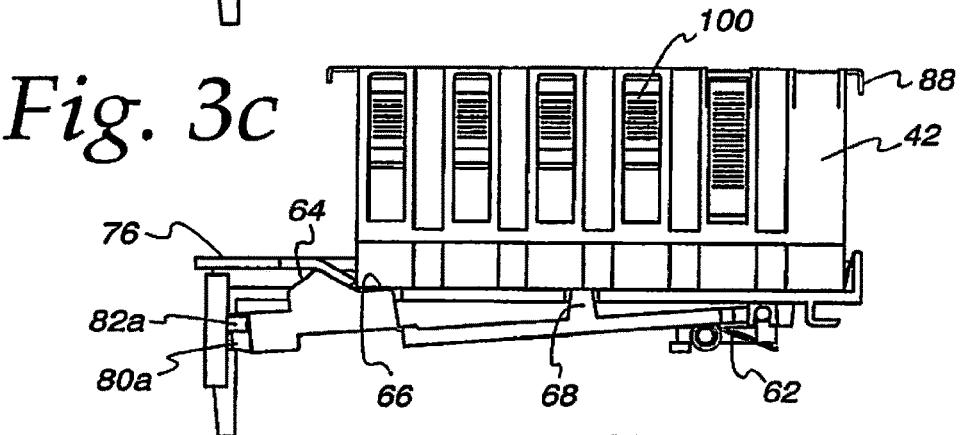
FIG. 3c is a side view of a load platform location with a sample carrier loaded thereon.
Figure 3D:
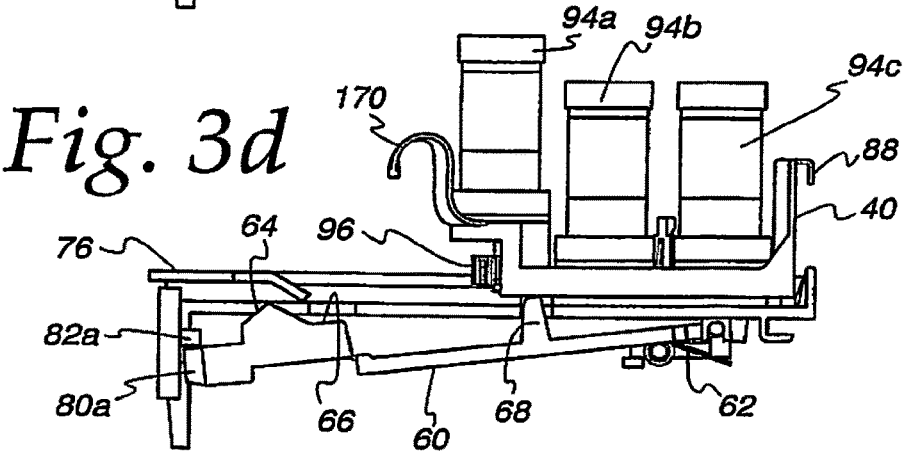
FIG. 3d is a side view of a load platform location with a reagent carrier loaded thereon.
Figure 4A:
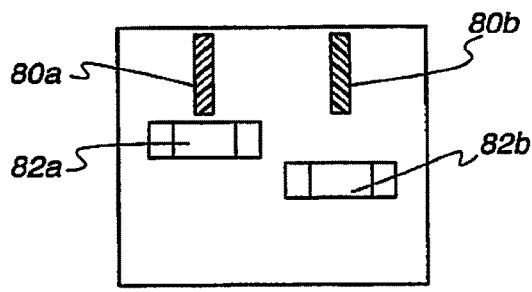
FIG. 4a is a cross-sectional view taken along line 4-4 of FIG. 3a illustrating detection of the FIG. 3a position of the position indicator.
Figure 4B:
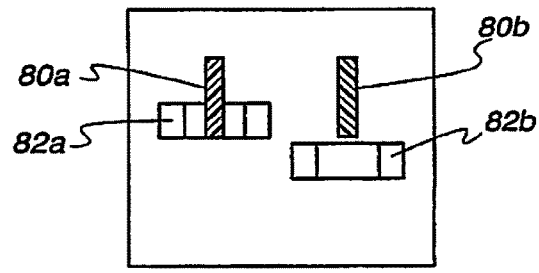
FIG. 4b is a cross-sectional view similar to FIG. 4a but with the position indicator in the position of FIG. 3b.
Figure 4C:
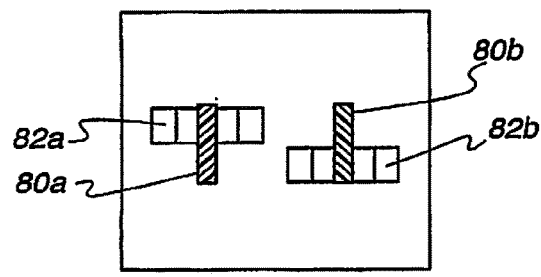
FIG. 4c is a cross-sectional view similar to FIG. 4a but with the position indicator in the position of FIG. 3c.
Figure 4D:
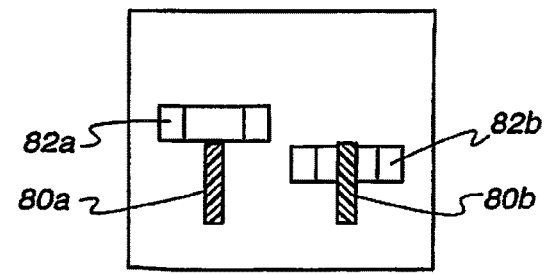
FIG. 4d is a cross-sectional view similar to FIG. 4a but with the position indicator in the position of FIG. 3d.

In the upper position of the position indicator 60, with no carrier 40, 42 present at the platform location as illustrated in FIG. 3a, the two ears 80a, 80b are both above the proximity sensors 82a, 82b (see FIG. 4a) which therefore detect nothing. The computer control may thus be provided a binary signal which simply indicates no carrier 40, 42 at that location 54.

If a carrier 40, 42 is loaded but not fully inserted into the location 54, it will either rest on the first set of knuckles 64 or (with a further but not fully inserted reagent carrier 40) partially push down on the third set of knuckles 68 as illustrated in FIG. 3b. In this partially lowered position, one ear 80a is proximate its associated proximity sensor 82a and the other ear 80b is still spaced from its associated proximity sensor 82b (see FIG. 4b), generating a signal indicating that a carrier 40, 42 has been placed in the location 54 but is not properly loaded.

If a sample carrier 42 is properly inserted into the location 54, it will rest on the second set of knuckles 66 (see FIG. 3c) and push the position indicator 60 down still further, whereby both ears 80a, 80b will be detected to be proximate their associated proximity sensors 82a, 82b (see FIG. 4c) and generate an appropriate signal indicative of that condition.

Finally, if a reagent carrier 40 is properly inserted into the location 54, it will rest on the third set of knuckles 68 (see FIG. 3d) and push the position indicator 60 down still further, whereby only the other ear 80b will be detected to be proximate its associated proximity sensors 82b (see FIG. 4d) and generate an appropriate signal indicative of that condition.

Status indicator lights 82, 84 (see FIGS. 1 and 2) may also be advantageously provided on the front of the load platform 30, with such lights 82, 84 associated with each location 54 and providing a clear visual indication of the status of each location to an operator. For example, when a location 54 is open, neither light 82, 84 associated with that position is lit, signifying to an operator that they may manually load a carrier 40, 42 at that location 54 if they desire. When a carrier 40, 42 is properly loaded at that location 54, one light 82 may be illuminated a suitable color (e.g., green). When a carrier 40, 42 is associated with a particular location 54 but is not at that location 54 at that time (e.g., if it is being moved to the bar code reader 46 for identification), the other light 84 associated with that location 54 may be illuminated a suitable color (e.g., amber or yellow) to warn an operator not to place another carrier 40, 42 in that location. Further, if a carrier 40, 42 is improperly loaded in a particular location 54, the indicator lights 82, 84 may advantageously be illuminated (e.g., by flashing on and off) to draw the attention of the operator to fix the problem.

Once a carrier 40, 42 has been properly loaded and detected at a platform location 54, it may then be automatically handled by the handling device 22.

Specifically, the transporter 38 with a gripper device 86 such as illustrated particularly in FIG. 6 of U.S. Pat. No. 6,588,625 B2 is positioned for movement behind the load platform 30. (The full disclosure of U.S. Pat. No. 6,588,625 B2 is hereby incorporated by reference.) The transporter 38 may, for example, be moved from a base position by a suitable drive such as a stepper motor to align its gripper device 86 with a support tab 88 (see, e.g., FIGS. 3b to 3d) of a carrier 40, 42 at a selected platform location 54. For example, the gripper device 86 may be positioned beneath the support tab 88 and then raised up so as to capture the tab 88 in the gripper device 86 (see, e.g., FIGS. 9a and 9b) and thereby pick up the carrier 40, 42 to carry it with the transporter 38. Such operation is illustrated in FIGS. 5a to 5h.

Figure 5A:
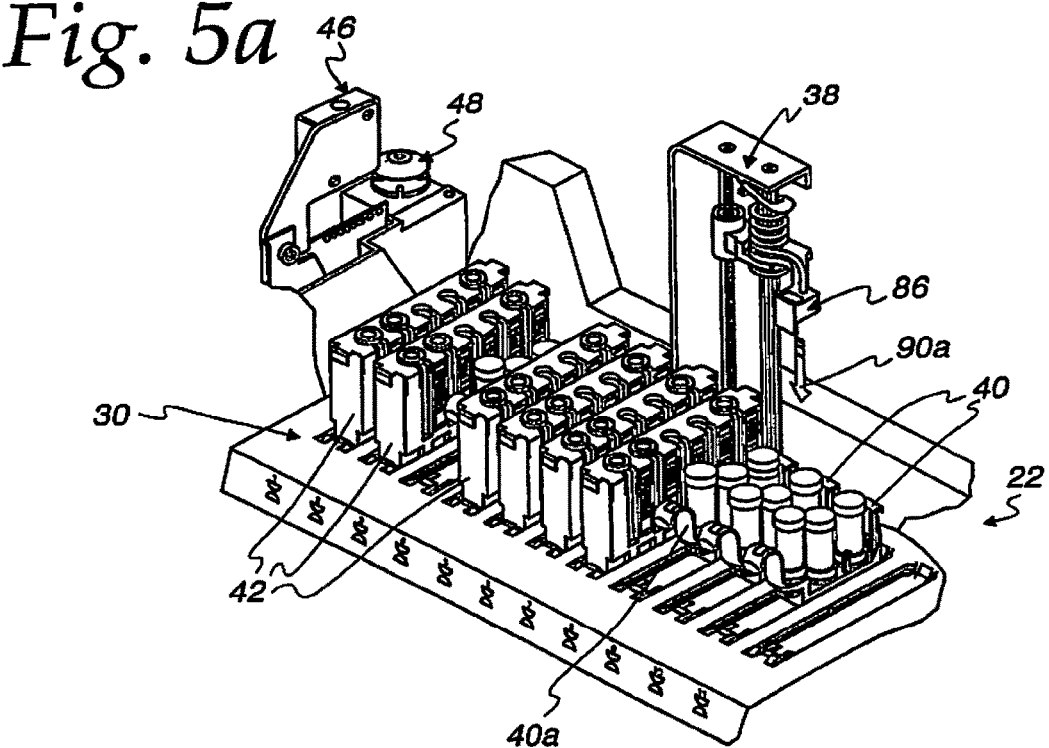
FIGS. 5a to 5f illustrate sequential operation a portion of the handling device of the present invention, with a reagent carrier being moved from a load platform by a transporter for identification by a bar code reader and then away from the bar code reader toward the carousel of the handling device.
Figure 5B:
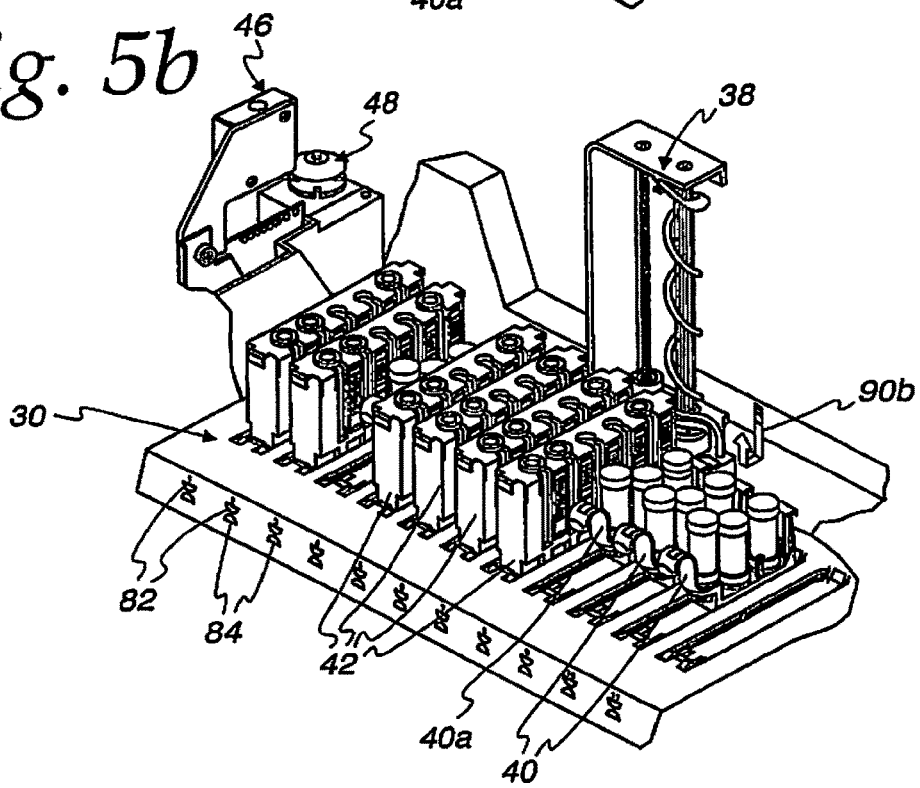
Figure 5C:
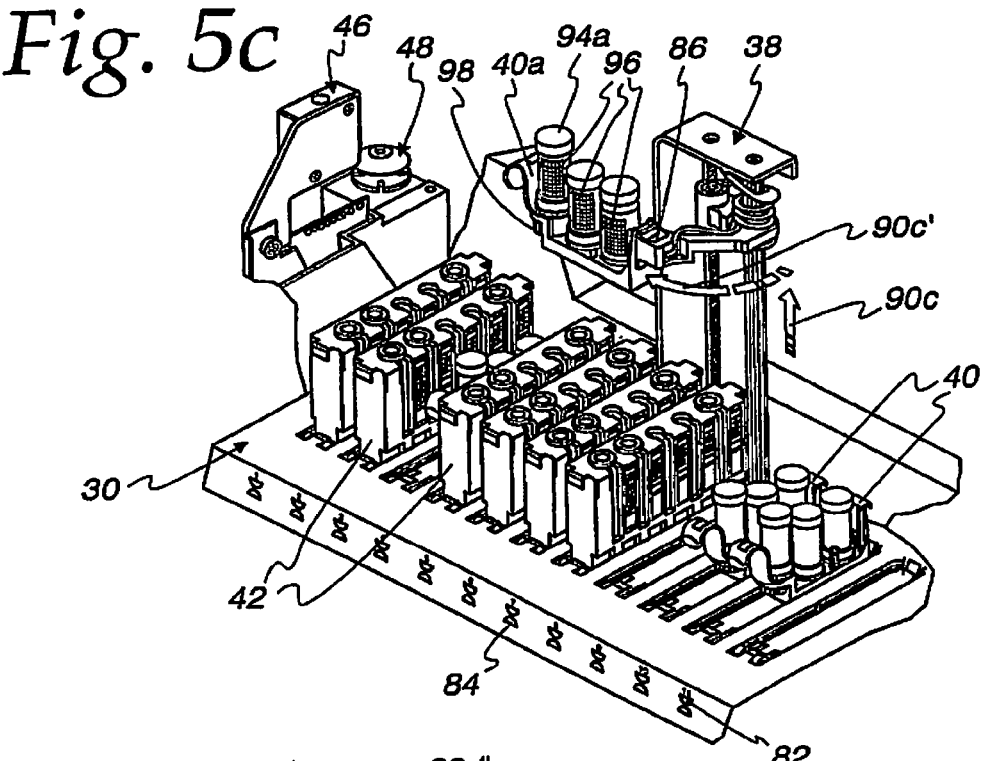
Figure 5D:
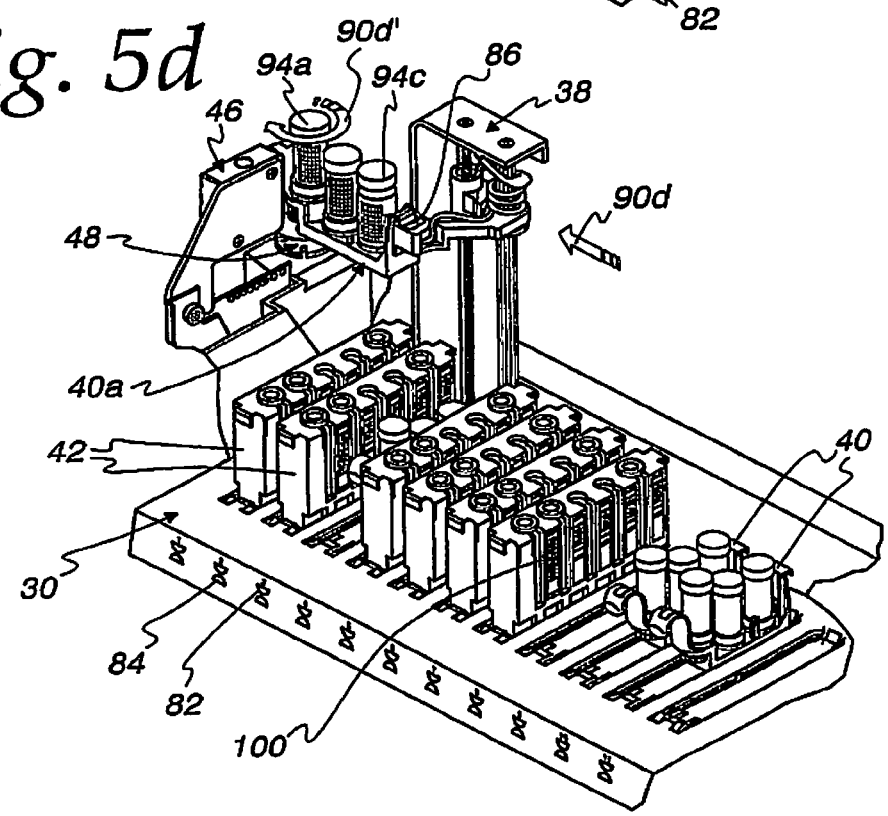

More particularly, in FIG. 5a, the transporter 38 is positioned with the gripper device 86 behind one of the reagent carriers 40a. As indicated by the motion arrows 90a and 90b in FIGS. 5a and 5b, the gripper device 86 is first lowered and then moved forward to a position beneath the carrier support tab 88, and then is raised to lift the reagent carrier 40a from the load platform 30. Once raised clear of (i.e., above) the other carriers 40, 42 on the platform 30 (see arrow 90c), the transporter 38 pivots to a position such as indicated by the arrow 90c' in FIG. 5c and then the transporter 38 is moved to the bar code reader 46 (see arrow 90d in FIG. 5d) whereby the reagent containers 94a, 94b, 94c are sequentially moved past the reader 46 for reading identifying bar codes 96 on the containers 94a-94c.

The reagent containers 94a-94c may be advantageously secured to the carrier 40 by bottle seats 95 or other suitable retention structures (e.g., retention tabs) to securely hold the containers 94a-94c thereon by, for example, friction or a snap-fit, depending upon the container 94a-94c. In accordance with one feature of the present invention, however, it should be appreciated that the container 94a should be secured relative to its bottle seat 95 so that it will rotate therewith.

As described in further detail hereinafter, at least one of the reagent containers 94a may be suitably secured to the carrier 40 so as to pivot with a drive gear 98 which is positioned on the bottom side of the reagent carrier 40. When that container 94a is positioned adjacent the bar code reader 46 for reading of its bar code (see FIG. 5d), the motor drive 48 may be advantageously engaged with the drive gear 98 so as to cause the drive gear 98 and attached bottle seat 95 and reagent container 94a to rotate as indicated by arrow 90d=.

This provides for particularly reliable bar code reading for containers (i.e., containers 94a containing reagents with microparticles) which may otherwise be difficult to read, as it ensures that the bar code 96 will at some point be properly oriented relative to the bar code reader 46 for proper reading. For example, shorter containers, which may require that the bar code 96 be wrapped around a cylindrical container rather than extending the height of the container 94, can advantageously be read in this manner. In fact, it should be appreciated that while the figures illustrate container 94a as being generally the same height at the other reagent containers 94b-94c, the container 94a, which is subject to being rotated, can advantageously be of a lesser height than those other containers 94b-94c, allowing not only for compact size where reagent containers 94a-94c advantageously store different reagent quantities (based, e.g., on testing requirements), but also allowing for a uniform top of all carried containers 94a-94c.

While the drive gear 98 may be a pinion type gear as discussed further hereinafter, the motor drive 48 adjacent the bar code reader 46 need not mesh with the gear teeth, but instead may advantageously consist of a resilient tapered disk, such as a conical rubber disk, which may be brought into frictional engagement with the bottom outer edge of the gear 98 (e.g., by lowering the carrier 40a onto the conical rubber disk when the carrier 40 is present for reading the bar code 96 of that container 94a). Such a drive 48 may thereby suitably engage the gear 98 to cause the desired rotation while the container 94a is being read.

Figure 5E:
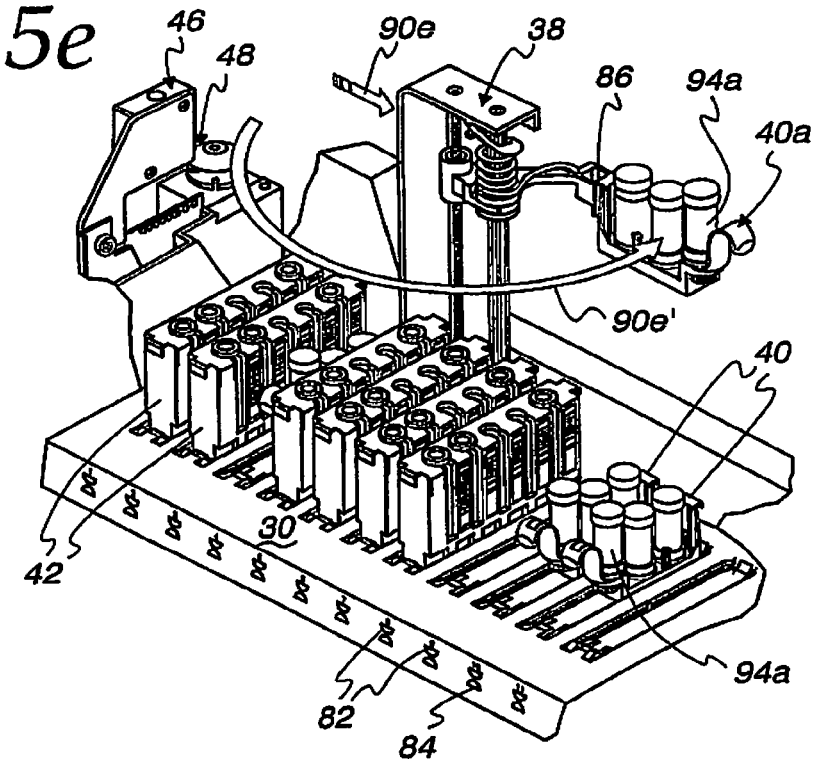

At this point, the computer control for the handling device 22 will have the identity of each reagent container 94a-94c, and the reagent carrier 40a may then move clear of the bar code reader 46 and pivot as indicated by arrows 90e and 90e' in FIG. 5e, respectively, and then be lowered and moved to the other end of the platform 30 as indicated by arrows 90f and 90f=, respectively, for storage on the carousel 34 as described hereinafter.

Movement of the sample carriers 42 from the platform 30 to the bar code reader 46 can be accomplished similar to the movement illustrated in FIGS. 5a to 5d, except that the motor drive 48 is not engaged and nothing is rotated on the sample carrier 42. Bar codes 100 for the samples can be provided on the carriers 42 and/or on the tubes of samples carried by the carriers 42, and the height generally is sufficient to permit the bar code 100 to extend the full height of the tube rather than being wrapped therearound.

Figure 5F:
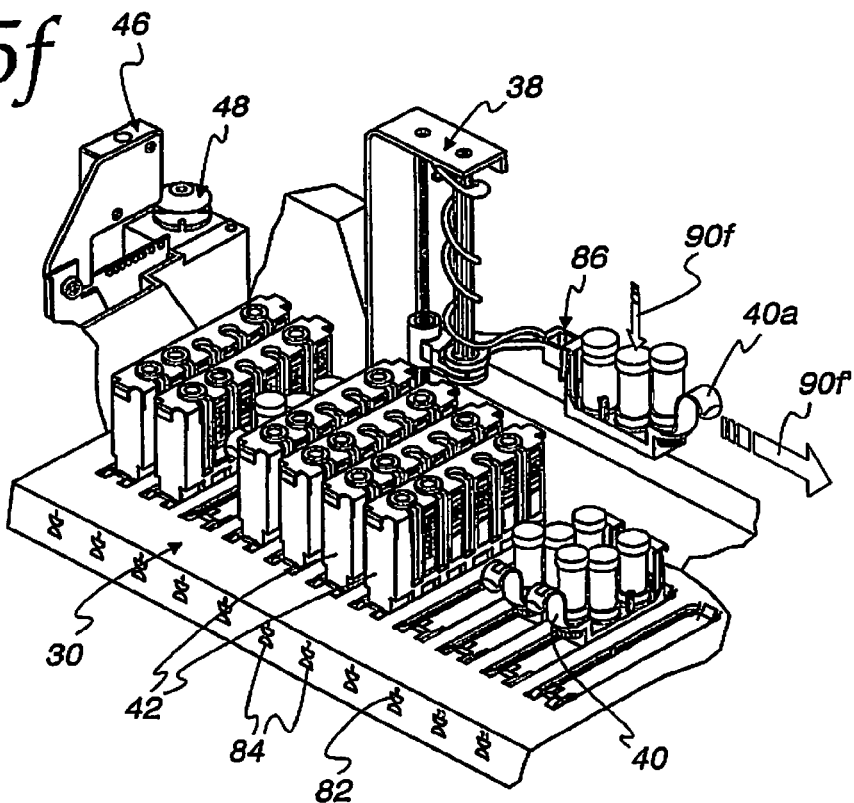
Figure 5G:
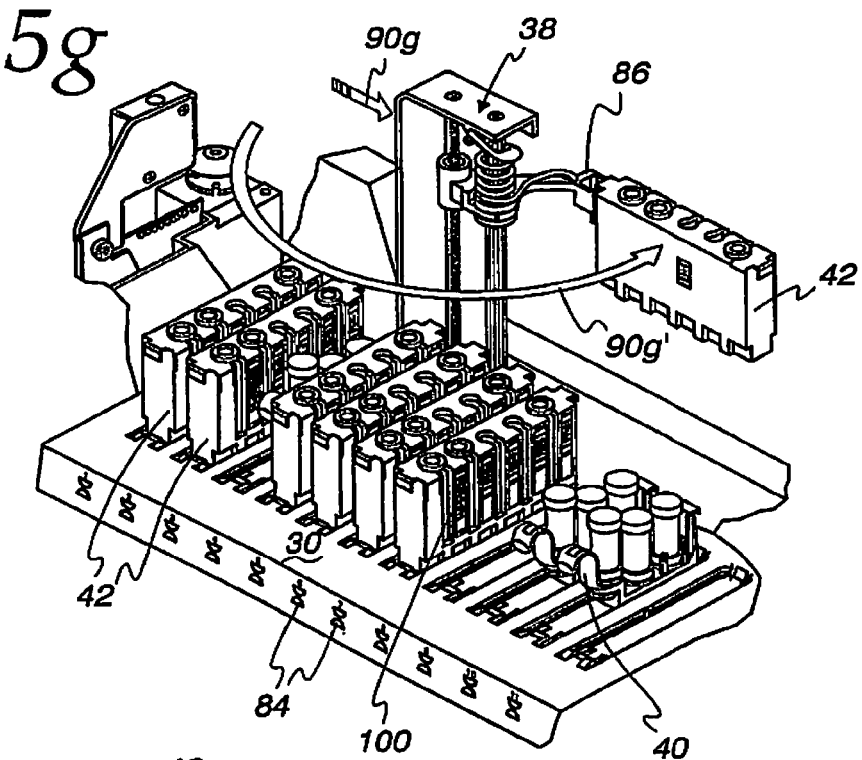
FIGS. 5g and 5h are similar to FIGS. 5e and 5f, and illustrate sequential operation of a portion of the handling device of the present invention, with a sample carrier being moved from the bar code reader to a transfer station.
Figure 5H:
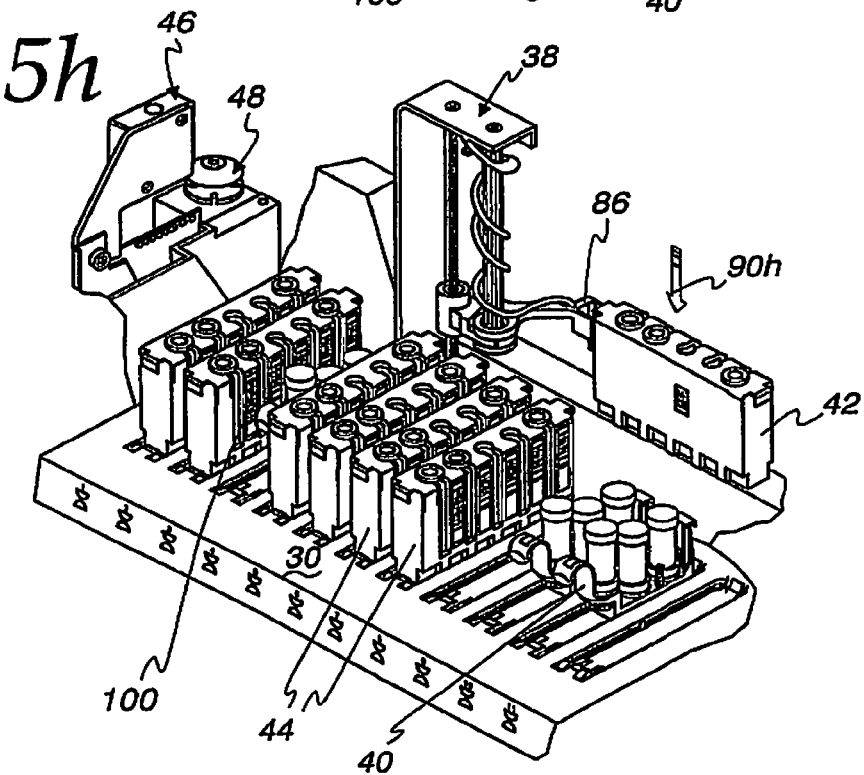

As illustrated in FIGS. 5g and 5h, once the sample bar codes 100 have been read to store the sample identifying information in the controlling computer, the sample carrier 42 can be cleared from the bar code reader 46 as indicated by arrows 90g and 90h (much as the reagent carrier 40 is cleared in FIG. 5e) and then either returned to a selected location 54 on the platform 30 to await further handling when the system 20 is ready to perform selected tests on it, or it can be placed in a ready position behind the platform 30 (see arrow 90h in FIG. 5h) where it is readily accessible to the pipettor or other suitable transfer device used to draw sample material and move it to the testing portion of the system 20.

Reference will now be had to FIGS. 6 to 10, which illustrate the carousel 34 on which a plurality of reagent carriers 40 may be stored, making the reagents carried thereon readily available when required for testing being performed by the system.

The carousel 34 is illustrated in FIG. 6 and defines a plurality of radial or spoke type carrier support locations therearound. The carousel 34 is suitably supported for rotation about a central vertical axis, as by the three wheels 110 having suitable grooves 112 (e.g., v-grooves) therein aligned in a horizontal plane. A central annular flange 114 is received in the grooves 112 around the outside of the three wheels 110 for supporting the carousel 34. One wheel 110a may be supported for rotation about an axis supported on a pivotable base 116 which is suitably biased outwardly, as by a spring 118, whereby the carousel 34 may be mounted for rotation by pulling the one wheel 110a inwardly to provide clearance while the flange 114 is first positioned in the grooves 112 of the other two wheels 110, after which the one wheel 110a can be released to also capture the flange 114 in its groove 112.

An annular gear 124 (see FIG. 7) is fixed to and extends down from the bottom of the carousel 34. A suitable drive 128, such as a stepper motor, drives a drive gear 130 (see FIG. 6) which engages with the carousel annular gear 124 to rotatably drive the carousel about its central axis and, moreover, to control its position. A suitable base position indicator 134 (see FIG. 6) can be provided on the carousel 34, such indicator 134 being suitably detectable in a specific location to locate the base position, with the stepper motor of the drive 128 controlled to incrementally drive the carousel 34 to selectively position the various carrier support locations as desired (as explained further hereinafter).

Various reagent carriers 40 are secured to the carousel 34 at selected or known support locations. Loading of such carriers 40 may be accomplished first in accordance with the sequence illustrated in FIGS. 5a to 5f, wherein a reagent carrier 40 is loaded on the platform 30, is carried by the transporter 38 to the bar code reader 46 to automatically detect the reagents carried in the containers 94a-94c thereon, and is then carried by the transporter 38 to the carousel 34. Specifically, the transporter 38 carries an identified reagent carrier 40 to a port 140 in the carousel housing 50 (see FIG. 1) which can be open or, alternatively, can have a controllable door which opens and closes when access is required to transport a reagent carrier 40 into or out of the housing 50.

The housing port 140 is aligned with the carousel carrier support location, which is located at a specific position within the housing 50. Specifically, a magnetic proximity detector 142 is fixed inside the housing 50 at that position as described in greater detail hereinafter.

A ring gear 146 is fixedly mounted concentric with the axis of rotation of the carousel 34 to pivot the reagent containers 94a as further detailed herein.

Figure 7:
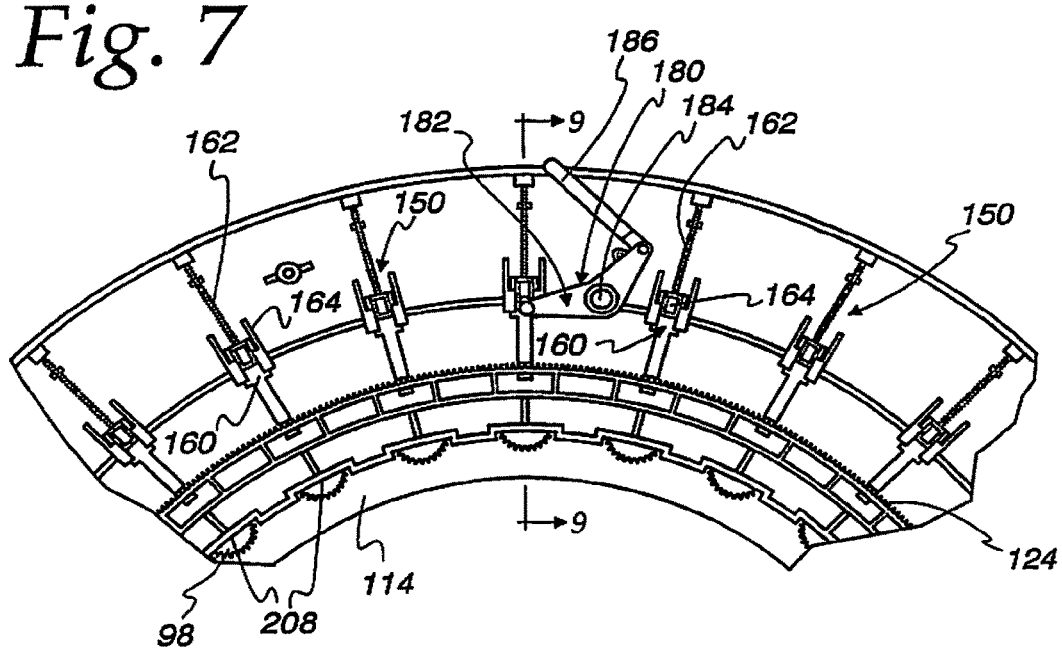
FIG. 7 is a bottom view of a portion of the carousel.
Figure 8:
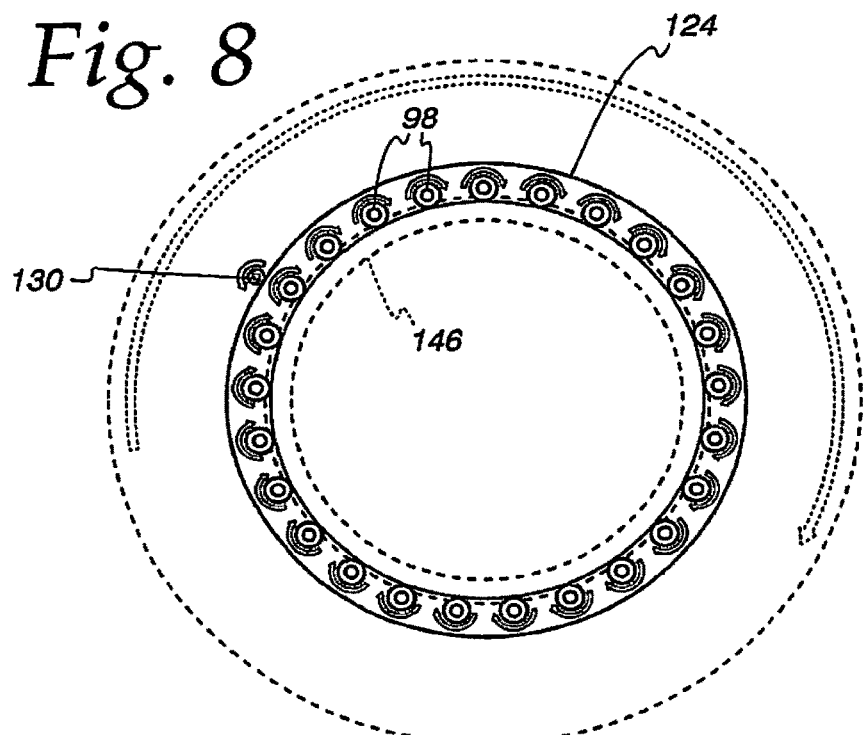
FIG. 8 is a schematic view illustrating the rotation of the carousel and related rotation of the reagent carrier drive gears.
Figure 10:
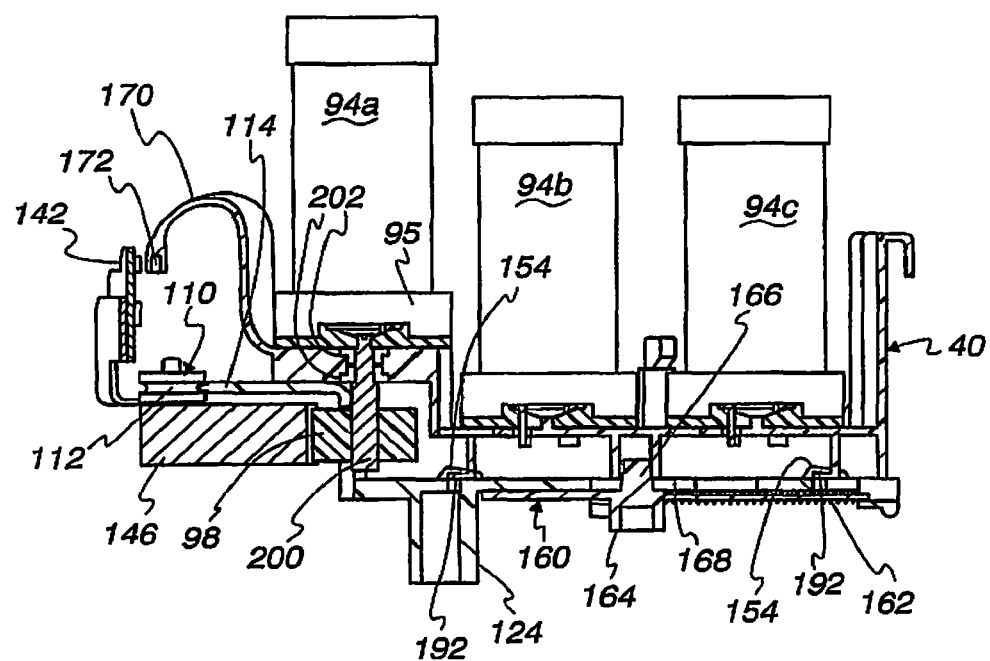
FIG. 10 is a cross-sectional view of a reagent carrier secured on the carousel.

As illustrated in FIGS. 6 and 7, each carousel carrier support location includes a connector 150 which includes a pair of raised portions 154 defining a pair of radially outwardly open pockets on top of the carousel 34. The support locations also each include a connecting or slide member 160 on the bottom side of the carousel 34 with a spring 162 biasing the slide member 160 radially inwardly (toward the center of the carousel 34). A bottom ear 164 extends downwardly from the slide member 160, and a top ear 166 extends through an opening 168 in the carousel 34 so as to project upwardly above the top surface of the carousel 34 (see FIGS. 6 and 9a-c).

As best illustrated in FIGS. 9a-c, the reagent carrier 40 has a finger tab 170 at the end opposite the support tab 88. It should be appreciated that the finger tab 170 can be advantageously and conveniently used by an operator to manually carry the carrier 40 to the platform 30 when initially loading the carrier 40 on the handling device 22. A suitable magnet 172 can be advantageously provided in the finger tab 170, which magnet 172 will be detected by the magnetic proximity detector 142 when proximate thereto (see, e.g., FIG. 10). Thus, when the proximity detector 142 is associated with the position at the housing port 140, the transporter 38 can be controlled so that it will not attempt to load a reagent carrier 40 on that carousel support location when a carrier 40 is already present there. That is, while ideally the computer control of the system 20 should know which carousel carrier support locations have a carrier 40 loaded thereon, to protect against possible damage to the system in the event of some computer control failure, the proximity detector 142 may be used as a backup to ensure that the transporter 38 does not attempt to force a carrier 40 onto a location where one is already present. Further, the proximity detector 142 may be used to help in aligning the carousel 34 so that a support location is properly aligned at the housing port 140.

Reference will now be had specifically to FIGS. 7 and 9*a-c* in connection with the loading of a reagent carrier 40 onto the carousel 34.

Specifically, the transporter 38 moves the carrier 40 after reading by the bar code reader 46 from the position shown in FIG. 5*f* to enter into the housing port 140. (It should be understood, however, that the carrier 40 may not be lowered as illustrated in FIG. 5*f*, but instead may be retained at the same height as illustrated in FIG. 5*e* during movement to the housing port 140.) As the transporter 38 reaches the loading position, it suitably engages a suitable release control 180 located at the housing port 140. In the illustrated embodiment, the release control 180 consists of a control arm 182 which is pivoted about a fixed post 184 as a result of pushing by the transporter 38 (or some carried component thereof) on an actuating arm 186 connected to one end of the control arm 182. A suitable spring or the like tends to bias the control arm 182 and actuating arm 186 in the opposite direction. The other end of the control arm includes a finger 188 which is aligned with the bottom ear 164 of the slide member 160 associated with the carrier support location positioned at the housing port 140. Pivoting of the control arm 182 will therefore cause the finger 188 to engage the bottom ear 164 of the slide member 160 and pull it radially outwardly against the biasing force of its spring 162. In that position (FIG. 9*b*), the transporter 38 will position the carrier 40 so that it is above the support location and a recess 190 in the bottom of the carrier 40 is located above the top ear 166 of the slide member 160, at which point the gripper device 86 may be lowered to release the support tab 88 and the transporter 38 retracted from the area of the housing port 140 (FIG. 9*c*).

When the transporter 38 leaves the area of the housing port 140, the release control 180 is no longer forced to pull on the slide member bottom ear 164, and therefore the slide member 160 is biased by its spring 162 to slide radially inwardly (toward the axis of the carousel 34). When this occurs, the slide member 160 through the engagement of its top ear 166 with the carrier recess 190 pulls the carrier 40 with it, and tabs 192 on the bottom of the carrier 40 are received in the pockets defined by the connector raised portions 154 to secure the carrier 40 to the carousel 34.

It should be appreciated that removal of a reagent carrier 40 may be conveniently and advantageously accomplished in a reverse order. Specifically, the transporter 38 can approach the housing port 140, engaging the release control 180 to pull the slide member 160 radially outwardly, and thereby also pull the carrier 40 (via the engagement of the top ear 166 with the carrier recess 190) outwardly, whereby the tabs 192 are out of the pockets defined by the connector 150. In that position, the carrier 40 essentially rests freely on the carousel 34 and may be picked up and removed therefrom by the transporter gripper device 186. The transporter 38 may then return the carrier 40 to the load platform 30, from which an operator may manually remove the carrier and either refill or replace the containers 94*a*-94*c* if appropriate.

FIGS. 6 and 9*a* to 10 more particularly illustrate a suitable carrier 40 and drive gear 98 assembly. Specifically, the drive gear 98 may be provided with an integral shaft 200 which extends through the platform of the carrier 40 and is suitably secured at its upper end for rotation with the bottle seat 95 thereabove (on which container 94*a* is supported). Suitable bearings 202 may be provided to facilitate rotation of the shaft 200 in the carrier platform.

Moreover, as illustrated in FIGS. 6-7 and 9*a*-10, a central opening 208 is provided at each carrier support location of the carousel 34 whereby the drive gear 98 of any carrier 40 secured to the carousel 34 projects inwardly through the openings 208 toward the central axis of the carousel 34. In such a position, the drive gears 98 of the secured carriers 40 will all engage the ring gear 146. As a result, when the carousel 34 is turned (i.e., by the drive gear 130 of drive 128), the carrier drive gears 98 will rotate around the ring gear 146 and thereby be caused to rotate in a planetary fashion as carried with the carousel 34. Thus, it should be appreciated that the carrier drive gear 98 may not only serve to facilitate proper bar code reading as previously described, but may also be used to rotate the containers 94*a* secured to the associated bottle seats 95. Such mixing can be particularly advantageous for some reagents such as those containing microparticles which might undesirably settle in the container 94*a* over time. Thus, it should be appreciated that even when not in use, the carousel 34 may be constantly rotated back and forth relatively slowly, somewhat like the action of a washing machine, to ensure that the reagents are maintained in the proper suspension.

When loaded, it should be appreciated that the carousel 34 will carry containers 94*a*-94*c* in three concentric rings about its central axis. The refrigerated compartment housing 50 may advantageously include three openings 220 (see FIG. 1) therethrough, with each opening 220 aligned with a different ring of containers 94*a*-94*c* stored therebeneath. Such openings can be used to provide access for the testing system 20 (e.g., its pipettor) to draw the desired reagent from the appropriate container 94*a*-94*c* (appropriately positioned beneath such openings 220 by the carousel 34) as required by the particular testing procedure being performed by the system 20.

It should be appreciated from the above description that the present invention may be used to provide particularly advantageous handling of reagents and samples in automatic testing systems.

Still other aspects, objects, and advantages of the present invention can be obtained from a study of the specification, the drawings, and the appended claims. It should be understood, however, that the present invention could be used in alternate forms where less than all of the objects and advantages of the present invention and preferred embodiment as described above would be obtained.

What is claimed is:
1. An apparatus comprising:
a loading platform of a diagnostic analyzer, the loading platform having a slot to receive a carrier;
a sensor to detect a presence of the carrier in the slot, the sensor including:
an arm pivotably coupled to the loading platform, the arm extending at least partially into the slot, the arm pivoted when the carrier is disposed in the slot and engages the arm; and an optical detector to detect a position of the arm and determine a presence or absence of the carrier based on the position of the arm; and a status indicator that provides a first display when the carrier is not present in the slot and provides a second display when the sensor detects the carrier in the slot.

2. The apparatus of claim 1, wherein the arm is pivotably coupled to a bottom side of the loading platform.

3. The apparatus of claim 1, wherein the arm is to be in an upward position when the carrier is not present in the slot and the arm is to be in a downward position when the carrier is in the slot.

4. The apparatus of claim 3, wherein the arm is biased in the upward position via a spring.

5. The apparatus of claim 4 further including an opening defined in a bottom wall of the loading platform at the slot, wherein a knuckle of the arm is to extend through the opening into the slot in the upward position.

6. The apparatus of claim 1, wherein the status indicator is located on a front side of the loading platform accessible by an operator.

7. The apparatus of claim 1, wherein the status indicator includes a light.

8. The apparatus of claim 7, wherein the light is not illuminated in the first display.

9. The apparatus of claim 8, wherein the light is illuminated in the second display.

10. The apparatus of claim 9, wherein the status indicator further provides a third display when the carrier has been retrieved from the slot and is being processed by the diagnostic analyzer.

11. The apparatus of claim 10, wherein the light is illuminated a first color in the second display, and wherein the light is illuminated a second color different than the first color in the third display.

12. The apparatus of claim 7, wherein the status indicator includes a first light of a first color and a second light of a second color different than the first color, and the status indicator provides a third display when an error occurs with the carrier, wherein the first light and the second light are illuminated in the third display.

13. A method comprising:
detecting, via a sensor, when a carrier has been inserted into a slot of a loading platform on a diagnostic analyzer, the sensor including:
an arm pivotably coupled to the loading platform, the arm extending at least partially into the slot, the arm pivoted when the carrier is disposed in the slot and engages the arm; and
an optical detector to detect a position of the arm and determine a presence or absence of the carrier based on the position of the arm; and
changing a display of a status indicator from a first display to a second display when the carrier is detected by the sensor in the slot.

14. The method of claim 13, wherein the arm is pivotally coupled to an underside of the loading platform.

15. The method of claim 13, wherein the status indicator includes a light, the method further including not illuminating the light in the first display and illuminating the light in the second display.

16. The method of claim 15 further including:
retrieving, via a robot, the carrier from the slot to be used in a diagnostic analysis;
detecting, via the sensor, when the carrier has been removed from the slot; and
changing the display of the status indicator from the second display to a third display when the sensor detects the carrier is removed from the slot.

17. The method of claim 16, wherein the light is to be illuminated a first color in the second display, the method further including illuminating the light a second color different than the first color in the third display.

* * * * *